(12) United States Patent
Govari

(10) Patent No.: US 6,484,118 B1
(45) Date of Patent: Nov. 19, 2002

(54) ELECTROMAGNETIC POSITION SINGLE AXIS SYSTEM

(75) Inventor: Assaf Govari, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 148 days.

(21) Appl. No.: 09/620,316

(22) Filed: Jul. 20, 2000

(51) Int. Cl.$^7$ .............................................. G06F 15/00
(52) U.S. Cl. ........................................ 702/150; 702/94
(58) Field of Search ...................... 600/424; 73/304 C; 702/150

(56) References Cited

U.S. PATENT DOCUMENTS

| | | | |
|---|---|---|---|
| 3,644,825 A | 2/1972 | Davis, Jr. et al. | 324/41 |
| 3,868,565 A | 2/1975 | Kuipers | 324/34 R |
| 4,017,858 A | 4/1977 | Kuipers | 343/100 R |
| 4,054,881 A | 10/1977 | Raab | 343/112 EA |
| 4,287,809 A | 9/1981 | Egli et al. | 89/41 |
| 4,317,078 A | 2/1982 | Weed et al. | 324/208 |
| 4,416,289 A | 11/1983 | Bresler | 128/737 |
| 4,526,177 A | 7/1985 | Rudy et al. | 128/737 |
| 4,560,930 A | 12/1985 | Kouno | 324/207 |
| 4,605,897 A | 8/1986 | Gelinas | |
| 4,613,866 A | 9/1986 | Blood | 343/448 |
| 4,642,786 A | 2/1987 | Hansen | 364/559 |
| 4,651,436 A | 3/1987 | Gaal | 33/533 |
| 4,710,708 A | 12/1987 | Rorden et al. | 324/207 |
| 4,771,237 A | 9/1988 | Daley | |
| 4,849,692 A | 7/1989 | Blood | 324/208 |
| 4,905,698 A | 3/1990 | Strohl, Jr. et al. | 128/653 R |
| 4,945,305 A | 7/1990 | Blood | 324/207.17 |

(List continued on next page.)

FOREIGN PATENT DOCUMENTS

| | | |
|---|---|---|
| JP | 10094609 | 4/1998 |
| WO | WO 92/03090 | 3/1992 |
| WO | WO 94/04938 | 3/1994 |
| WO | WO 94/23647 | 10/1994 |
| WO | WO 96/05768 | 2/1996 |
| WO | WO 96/41119 | 12/1996 |
| WO | WO 97/29678 | 8/1997 |
| WO | WO 97/29679 | 8/1997 |
| WO | WO 97/29709 | 8/1997 |
| WO | WO 97/29710 | 8/1997 |
| WO | WO 97/32179 | 9/1997 |
| WO | WO 97/42517 | 11/1997 |
| WO | WO 98/36236 | 8/1998 |
| WO | WO 99/32033 | 7/1999 |
| WO | WO 99/52430 | 4/2000 |

OTHER PUBLICATIONS

John David Jackson, "Classical Electrodynamics", 2nd edition, John Wiley & Sons, pp. 177–179.

William Press et al., "Numerical Recipes in C, the Art of Scientific Computing", 2nd edition, Cambridge University Press, pp. 383–393.

Primary Examiner—John S. Hilten
Assistant Examiner—Xiuqin Sun
(74) Attorney, Agent, or Firm—Frederick L. Herman; Louis J. Capezzuto

(57) ABSTRACT

A system for determining the position of a medical device having a sensor comprises a plurality of field radiators wherein each field radiator has a plurality of radiator elements. Each radiator element generates a magnetic field such that each magnetic field is distinct from one another due to the use of a different frequency through simultaneous energizing of the radiator elements. A signal processor is operatively connected to the field radiators and the sensor of the medical device for receiving a sensing signal from the sensor indicative of the magnetic field sensed at the sensor. Alternative field radiator arrangements are also provided in conjunction with a novel algorithm utilizing a global convergent technique.

31 Claims, 15 Drawing Sheets

U.S. PATENT DOCUMENTS

| | | | |
|---|---|---|---|
| 5,002,137 A | 3/1991 | Dickinson et al. | 175/19 |
| 5,042,486 A | 8/1991 | Pfeiler et al. | 128/653 R |
| 5,068,608 A | 11/1991 | Clark, Jr. | 324/220 |
| 5,099,845 A | 3/1992 | Besz et al. | 128/653.1 |
| 5,172,056 A | 12/1992 | Voisin | 324/207.17 |
| 5,211,165 A | 5/1993 | Dumoulin et al. | 128/653.1 |
| 5,251,635 A | 10/1993 | Dumoulin et al. | 128/653.1 |
| 5,253,647 A | 10/1993 | Takahashi et al. | 128/653.1 |
| 5,255,680 A | 10/1993 | Darrow et al. | 128/653.1 |
| 5,258,766 A * | 11/1993 | Murdoch | 600/424 |
| 5,265,610 A | 11/1993 | Darrow et al. | 128/653.1 |
| 5,269,289 A | 12/1993 | Takehana et al. | 128/4 |
| 5,273,025 A | 12/1993 | Sakiyama et al. | 128/6 |
| 5,274,328 A | 12/1993 | Begin et al. | |
| 5,309,913 A | 5/1994 | Kormos et al. | 128/653.1 |
| 5,325,873 A | 7/1994 | Hirschi et al. | 128/899 |
| 5,375,596 A | 12/1994 | Twiss et al. | 128/653.1 |
| 5,377,678 A | 1/1995 | Dumoulin et al. | 128/653.1 |
| 5,391,199 A | 2/1995 | Ben-Haim | 607/122 |
| 5,425,367 A | 6/1995 | Shapiro et al. | 128/653.1 |
| 5,425,382 A | 6/1995 | Golden et al. | 128/899 |
| 5,429,132 A | 7/1995 | Guy et al. | 128/653.1 |
| 5,437,277 A | 8/1995 | Dumoulin et al. | 128/653.1 |
| 5,443,489 A | 8/1995 | Ben-Haim | 607/115 |
| 5,453,687 A | 9/1995 | Zierdt et al. | 324/207.17 |
| 5,553,611 A | 9/1996 | Budd et al. | |
| 5,558,091 A | 9/1996 | Acker et al. | 128/653.1 |
| 5,577,502 A | 11/1996 | Darrow et al. | 128/653.1 |
| 5,622,169 A | 4/1997 | Golden et al. | 128/653.1 |
| 5,629,621 A | 5/1997 | Goldfine et al. | |
| 5,644,229 A | 7/1997 | Dossel et al. | |
| 5,646,524 A | 7/1997 | Gilboa | 324/207.17 |
| 5,682,886 A | 11/1997 | Delp et al. | 128/653.1 |
| 5,694,945 A | 12/1997 | Ben-Haim | 128/736 |
| 5,715,822 A | 2/1998 | Watkins et al. | 128/653.5 |
| 5,729,129 A | 3/1998 | Acker et al. | 324/207.12 |
| 5,752,513 A | 5/1998 | Acker et al. | 128/653.1 |
| 5,769,843 A | 6/1998 | Abela et al. | 606/10 |
| 5,797,849 A | 8/1998 | Vesely et al. | 600/461 |
| 5,879,297 A | 3/1999 | Haynor et al. | 600/407 |
| 5,899,860 A | 5/1999 | Pfeiffer et al. | |
| 5,913,820 A | 6/1999 | Bladen et al. | 600/407 |
| 5,997,473 A | 12/1999 | Taniguchi et al. | 600/117 |
| 6,016,697 A * | 1/2000 | McCulloch et al. | 73/304 C |
| 6,073,043 A * | 6/2000 | Schneider | 600/424 |
| 6,129,668 A * | 10/2000 | Haynor et al. | 600/424 |
| 6,314,310 B1 * | 11/2001 | Ben-Haim et al. | 600/424 |

* cited by examiner

ELECTROMAGNETIC POSITION SINGLE AXIS SYSTEM

FIELD OF THE INVENTION

The present invention relates generally to object tracking systems, and specifically to non-contact, electromagnetic medical systems and methods for tracking the position and orientation of an object. The present invention is also directed to a novel calibration method for electromagnetic-based medical tracking systems that can account for the effects of interference from nonmoving metallic objects.

BACKGROUND OF THE INVENTION

Non-contact methods of determining the position of an object based on generating a magnetic field and measuring its strength at the object are well known in the art. For example, U.S. Pat. No. 5,391,199, and PCT patent application publication WO 96/05768, which are incorporated herein by reference, describe such systems for determining the coordinates of a medical probe or catheter inside the body. These systems typically include one or more coils within the probe, generally adjacent to the distal end thereof, connected by wires to signal processing circuitry coupled to the proximal end of the probe.

U.S. Pat. No. 4,710,708, which is incorporated herein by reference, describes a location determining system using a single axis solenoid with a ferromagnetic core as a radiating coil. There are a plurality of magnetic coil receivers. The position of the solenoid is determined assuming that it radiates as a dipole.

PCT patent application publication WO 94/04938, which is incorporated herein by reference, describes a position-finding system using a single sensing coil and an array of three, three-coil radiators. The radiator coils are wound on non-ferromagnetic forms. The position of the sensing coil is determined based on a dipole approximation to the magnetic fields of the coils where an estimate of the orientation of the sensor coil is first utilized in order to determine the position of the sensor coil in that order. Additionally, the radiator coils of each array are energized sequentially using a time multiplexing approach. Interestingly, although this reference discloses that frequency multiplexing can be utilized in order to significantly increase the operating speed of the position system, it clearly indicates that there are disadvantages to this type of approach due to its complexity. It is also important to note that although this reference teaches a single axis sensor position and orientation tracking system, it does not address any specific method for calibrating the system.

Accordingly, to date, there is no known system or method that provides for a electromagnetic position sensor single axis system and method that is capable of being simultaneously driven through frequency multiplexing utilizing a novel exact solution technique and a novel calibration method.

SUMMARY OF THE INVENTION

The present invention is a novel system and method used for determining the position and orientation of a medical device having a single sensor arranged along the longitudinal axis of the device. The system comprises a plurality of field radiators wherein each field radiator has a plurality of radiator elements. Each radiator element generates a magnetic field that is distinct from the others through its frequency which is sometimes referred to as "frequency multiplexing". A signal processor is operatively connected to the field radiators and the sensor of the medical device for receiving a sensing signal from the sensor indicative of the magnetic field sensed at the sensor. The sensing signal defines a measured magnetic field at the sensor. The signal processor also has a desired range of accuracy for the system which is stored therein. The signal processor includes an initial position estimator for establishing an initial position estimate for the sensor (which is based on the dipole approximation); a magnetic field calculator for calculating the magnetic field at the initial position estimate; a steepest descent calculator for calculating a steepest descent of the calculated magnetic field to the measured magnetic field; and a new position estimate calculator for calculating a new position estimate of the sensor based on the steepest descent. The magnetic field estimator and the steepest descent calculator use the exact theoretical field expressions and pre-stored calibration data which are unique to the system. The signal processor determines the position of the sensor when the new position estimate of the sensor is within the desired range of accuracy for the system.

The system also includes pre-stored calibration information for use with the magnetic field calculator and the steepest descent calculator for calculation of the magnetic field and the steepest descent step respectively. This calibration data is uniquely derived for each system using a novel calibration system and method along with its unique algorithm. The system also has a predetermined and stored desired range of accuracy of <0.1 cm (the accuracy of the system). However, the incremental steps (iterations) for the algorithm are stopped as soon as the change from a previous step is less than 0.001 cm which is necessary in order to get better than 1 mm accuracy for the system.

One embodiment for the plurality of field radiators are arranged in a fixed arrangement and are contained in a fixed plane on a location pad. Other field radiator embodiments as described later do not necessarily have to lie in the same plane. In the first embodiment, the radiator elements of the field radiators are mutually orthogonal. In this embodiment, the system has three fixed radiators wherein each radiator has three generator elements or coils mutually orthogonal to each other.

Additionally, the signal processor determines both the position and orientation of the sensor such that the position of the sensor is derived in three different directions (X, Y, Z) and at least two orientations (pitch and yaw) which is generally known as 5 degrees of freedom (DOF). However, the restriction to 5 DOF is due to the coil sensor symmetry as shown. Thus, it is contemplated by the present invention to also provide for 6 DOF (X, Y, Z directions and three orientations roll, pitch and yaw) by changing the configuration of the sensor coil to an asymmetrical shape.

The system further comprises a display operatively connected to the signal processor for displaying the position and orientation of the sensor. Moreover, the display displays the position and the orientation of the sensor with respect to an anatomical feature of a patient. This is particularly useful for navigating a surgical instrument within a patient's anatomy for performing a surgical procedure. The system further utilizes a reference device, which can be an external removable patch, for establishing a frame of reference. One particular use of the system is to map the heart thereby creating a 3D model of the heart. The sensor can be used together with a physiological sensor, such as an electrode in order to map a physiological condition, for instance, a local activation time (LAT).

The present invention also includes a novel method of determining the position and orientation of a sensor relative to a plurality of field radiators of known location wherein each of the field radiators comprises a plurality of co-located radiator elements. Each radiator element produces a differentiable field from all other field generating elements through frequency multiplexing. The sensor produces sensing signals indicative of the magnetic field at the sensor and from which the field at said sensor may be calculated. The method comprises the steps of:

(a) establishing a desired range of accuracy;

(b) determining an initial estimate of sensor position and orientation;

(c) calculating the magnetic field at the estimated sensor position and orientation;

(d) calculating the steepest descent from the calculated magnetic field at the estimated sensor position and orientation to the measured field at the sensor;

(e) calculating a new estimate for said sensor position and orientation from the steepest descent;

(f) iterating steps (c)–(e) based on the newly calculated sensor position and orientation estimate of step (e) to refine the sensor position and orientation estimate.

As mentioned above, the desired range of accuracy for the single axis sensor position and orientation system is $\leq 0.1$ cm (the accuracy of the system). However, the incremental steps of the position and orientation algorithm are stopped as soon as the change from a previous step is less than 0.001 cm which is necessary in order to get better than 1 mm accuracy for the system. Additionally, the method includes establishing, storing and using of calibration information for the field radiators. This calibration information is derived using a novel calibration system and method. The calibration information is used at steps (c) and (d) for calculating a new estimate for the sensor position and orientation in order to provide greater accuracy to the system. The method also includes an optional step of refining the initial starting point of the sensor position and orientation using a dipole approximation in step (b).

The method further includes determining the position of the sensor in three different directions (X,Y,Z) and the orientation of the sensor in at least two orientations (pitch and yaw). Additionally, a display is used with this method for displaying the position and orientation of the sensor to include mapping this information to a displayed an anatomical feature of a patient which can be in the form of a pre-acquired image, real time image or model of the anatomy of interest.

The present invention also includes a novel calibration method which accounts for the effects of stationary metallic objects that are located within the mapping volume when the position and orientation medical system is in use. The novel calibration method is used for any medical system capable of generating a magnetic field for tracking a position of a medical device. The method comprising the steps of:

(a) defining a mapping volume within the generated magnetic field;

(b) placing a metallic object within the mapping volume;

(c) aligning a sensor at a first point within the mapping volume and measuring the magnetic field at the first point with the sensor to establish a first coordinate position ($X_i$, $Y_i$, $Z_i$);

(d) moving the sensor to a next point ($X_i$+dx, $Y_i$+dy, $Z_i$+dz) along one coordinate axis by an added distance component (dx, dy, dz) and measuring the magnetic field at the next point to establish a next coordinate position;

(e) interpolating the magnetic field at an intermediate point between the first position and the next coordinate position to establish an interpolated intermediate coordinate position;

(f) determining the position difference between the interpolated intermediate coordinate position and an actual intermediate coordinate position;

(g) comparing the position difference to an error limit;

(h) setting ($X_i$, $Y_i$, $Z_i$) of the next point as ($X_i=X_i$+dx, $Y_i=Y_i$+dy, $Z_i=Z_i$+dz) if the position difference is within the error limit and repeating steps (d)–(g) along another coordinate axis; and (i) setting the added distance component (dx, dy, dz) by decreasing the value of the added distance component if the position difference is not within the error limit and repeating steps (d)–(g) along the same coordinate axis.

The method also includes completing the calibration method for the entire mapping volume in accordance with the steps outlined above. Although, the error limit can be any reasonable error range, it is preferable that the error limit be $\leq 1$ mm for the greatest accuracy effects. Additionally, the sensor is stepped or moved a distance ranging from about 2 cm to about 3 cm. Moreover, with respect to the stepping of the sensor, the distance moved should remain constant to eliminate variability in the calibration. Also, step (i) is accomplished by decreasing the value of the added distance component through division by a factor of two ($X_i$+dx/2, $Y_i$+dy/2, $Z_i$+dz/2).

A second embodiment of the calibration method accounting for static metallic objects comprises the steps of:

(a) defining a mapping volume within the generated magnetic field;

(b) placing a metallic object within the mapping volume;

(c) aligning a sensor at a first point within the mapping volume and measuring the magnetic field at the first point with the sensor to establish a first coordinate position ($X_i$, $Y_i$, $Z_i$);

(d) extrapolating the magnetic field of a next point ($X_i$+dx, $Y_i$+dy, $Z_i$+dz) along one coordinate axis by an added distance component (dx, dy, dz);

(e) calculating the coordinate position at the extrapolated next point based on the extrapolated magnetic field to establish an extrapolated coordinate position;

(f) determining the position difference between the extrapolated coordinate position and the actual coordinate position of the next point;

(g) comparing the position difference to an error limit;

(h) setting the added distance component (dx, dy, dz) according to a predetermined distance if the position difference is within the error limit, aligning the sensor to a new point within the mapping volume along another coordinate axis and measuring the magnetic field at the new point with the sensor to establish a new point coordinate position and repeating steps (d)–(g) along the other coordinate axis; and (i) setting the added distance component (dx, dy, dz) by decreasing the value of the added distance component if the position difference is not within the error limit and establishing an intermediate point by repeating steps (d)–(g) along the same coordinate axis.

The predetermined distance may remain constant and is preferably approximately 3 cm. However, the predetermined distance or step distance can be varied by the user as well. Additionally, the added distance component can be decreased by a factor of two such that the intermediate point or position is defined as $(X_i+dx/2, Y_i+dy/2, Z_i+dz/2)$.

For either calibration embodiment accounting for the effects of stationary metallic objects, the sensor is moved according to the vertices of a cube and the entire mapping volume comprises a plurality of cubes. Each cube is defined by measurements derived from at least four different vertices. Generally, the calibration method is accomplished for a mapping volume is approximately 20 cm×20 cm×20 cm or $(20 \text{ cm})^3$. For controlled accuracy in the calibration, the sensor is moved by the arm of a robot.

These and other objects, features and advantages of the present invention will be more readily apparent from the detailed description set forth below, taken in conjunction with the accompanying drawings.

DESCRIPTION OF THE PREFERRED EMBODIMENTS

The present invention is a novel medical tracking system and method for determining the position and orientation of an object, such as a probe or catheter, utilizing a single axis position sensor and a novel position and orientation determination method. The system is also utilized with a novel calibration system and method.

Figure 1:
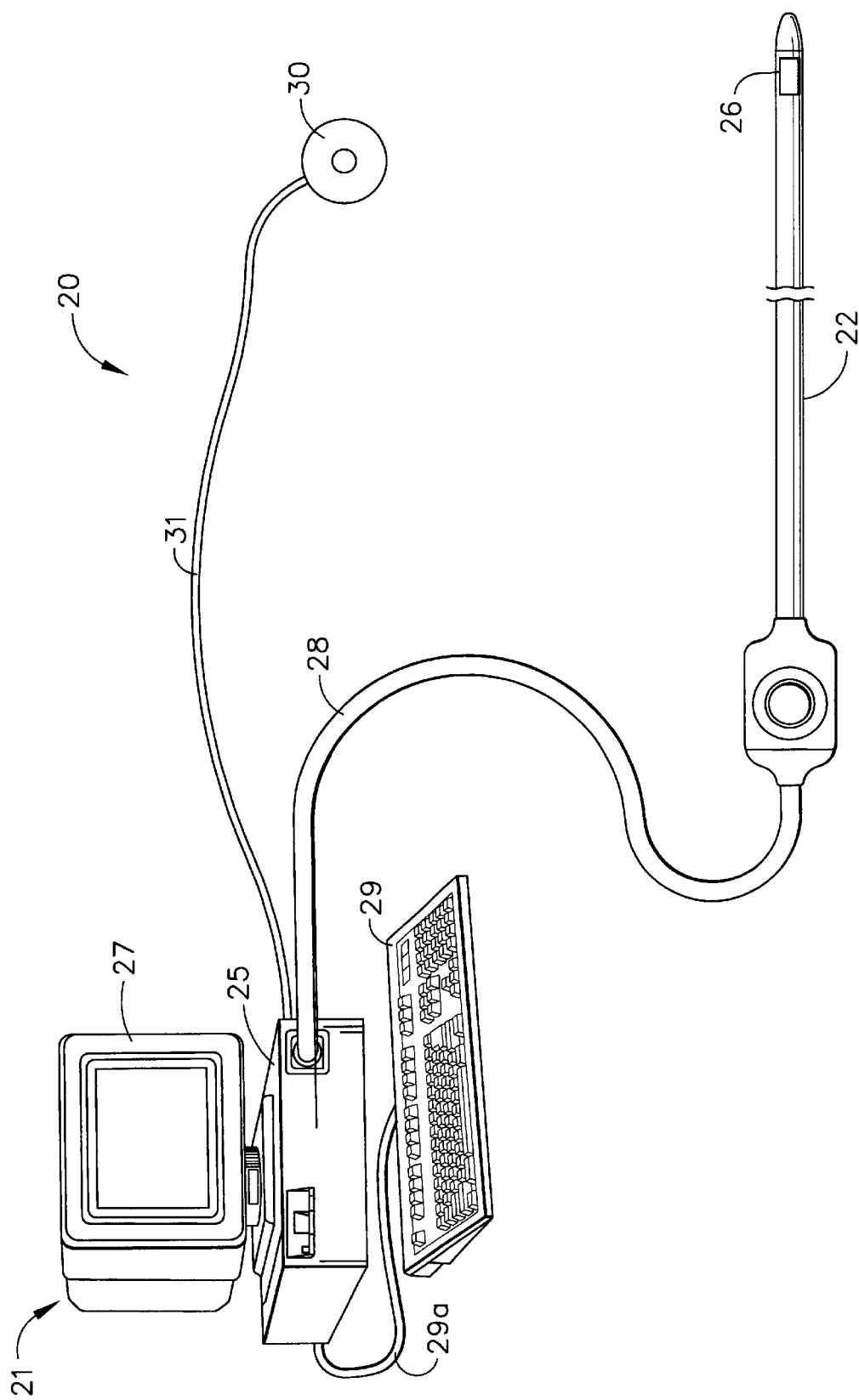
FIG. 1 is a perspective view of one embodiment of a position sensing system in accordance with the present invention.

One embodiment of a novel position and orientation system 20 according to present invention is shown in FIG. 1. The system 20 comprises a console 21, which enables the user to observe and regulate the functions of a peripheral medical device such as a probe or catheter 22. The catheter 22 is connected to the console 21 at a signal processor 25 (computer) by wire 28. The catheter 22 has a single position sensor 26 fixed near the distal end of the catheter 22 along the longitudinal axis of the catheter 22 wherein the position sensor 26 is operatively connected to the signal processor 25 by wire 28. Console 21 preferably includes that the signal processor (computer) 25 contains signal processing circuits which are typically self-contained inside the computer 25. A display 27 and keyboard 29 are operatively connected to the signal processor 25 wherein keyboard 29 is connected by wire 29a. The display 27 permits real-time display of the position and orientation of the catheter 22 at the position sensor 26. Display 27 is particularly useful for displaying position and orientation images and information of the position sensor 26 along with an image or model of particular anatomy such as an organ. One particular use of the system 20 is to map a heart thereby creating a 3D anatomical map of the heart. The position sensor 26 is used together with a physiological sensor, such as an electrode for mapping a physiological condition, e.g. LAT.

The signal processor 25 typically receives, amplifies, filters and digitizes signals from catheter 22, including signals generated by position sensor 26 whereupon these digitized signals are received and used by the signal processor 25 to compute the position and orientation of the catheter 22 at the position sensor 26.

The system 20 may also include a reference device 30, which also utilizes a position sensor (not shown), for establishing a frame of reference for the system 20. The reference device 30 is an external patch removably adherable to the exterior surface of a patient and is operatively connected to the signal processor 25 by wire 31. It is important to note that the reference device may consist of other alternative forms such as a second catheter or probe with position sensor for internal placement within a patient.

Figure 2:
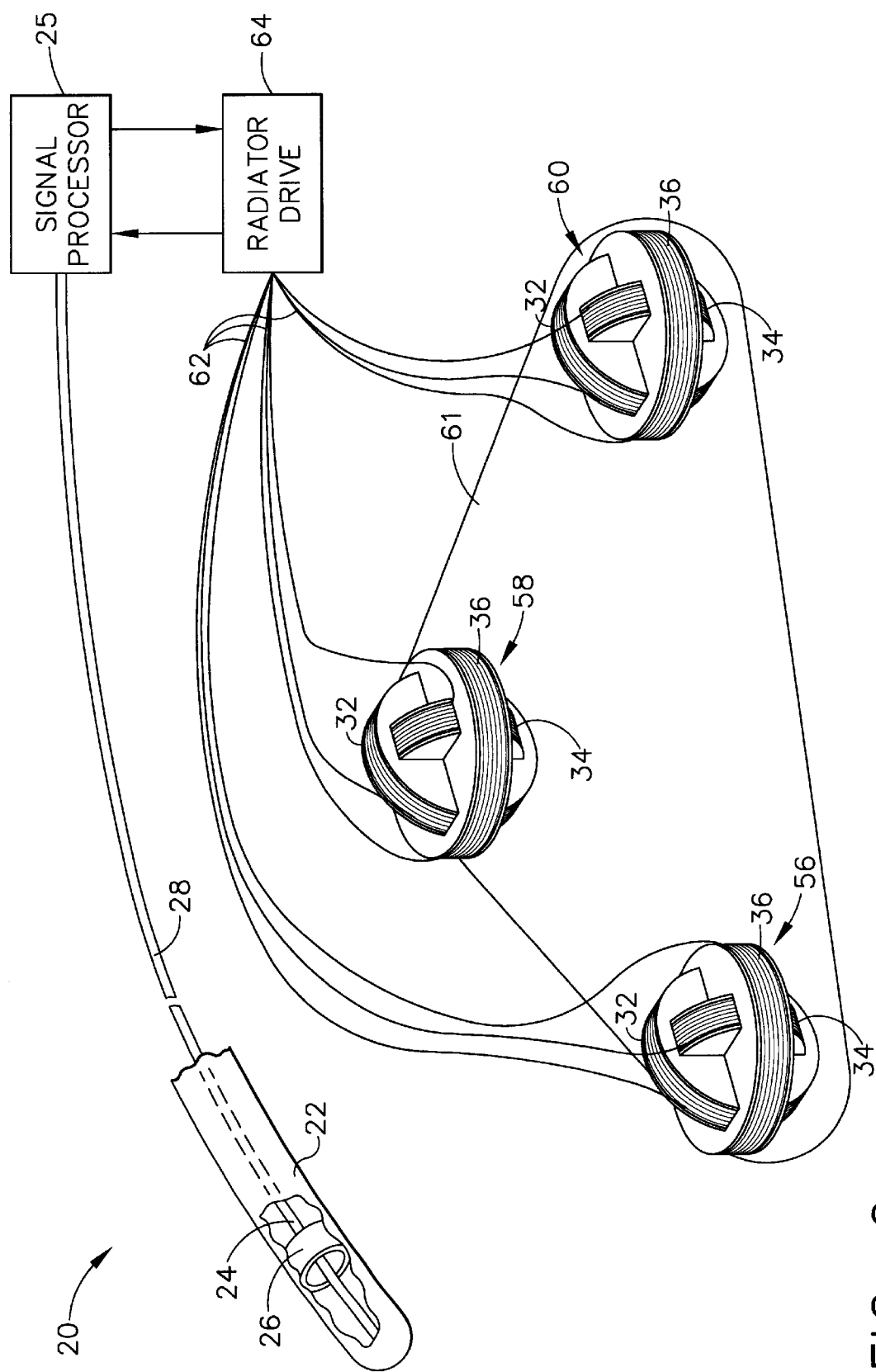
FIG. 2 is a schematic illustration of the position sensing components of FIG. 1.

Reference is now made to FIG. 2. which schematically illustrates the components of the position sensing system 20 responsible for determining the position and orientation of the catheter 22 at the position sensor 26. As shown, the position sensor 26 is in the form of a coil or hollow cylinder. However, other forms for the position sensor 26, such as barrel-shaped, elliptical-shaped, (to include asymmetrical shapes), etc., are also contemplated herein. It is also contemplated by the present invention that the sensor coil 26 can optionally include a flux concentrator as a core. Additionally, the sensor 26 may be in other forms rather than a coil, for instance, a magnetoresistive (MR) sensor, or a flux gate or hall effect sensor.

As illustrated and mentioned above, the position sensor 26 is in the form of a sensing coil and is positioned near the distal end of the catheter 22 such that the sensor coil 26 is preferably coaxial or along the longitudinal axis of the catheter 22. As defined herein the position sensor 26 can be optionally referred to as a position sensor, location sensor, position and orientation sensor, sensor coil, sensing coil, coil or like terminology. Preferably, catheter 22 has a lumen 24 which extends the length of catheter 22. Preferably, sensor coil 26 has a hollow core and is positioned within catheter 22 such that the axis of sensor coil 26 lies within lumen 24 and along or parallel to the axis of catheter 22. This construction provides access from the proximal end of the catheter 22 to its distal end through the hollow core of sensor coil 26, permitting the catheter 22 to be used as a delivery device for the delivery of any type of therapeutic through the sensor coil 26. Sensor coil 26 and lumen 24 permit the catheter 22 to be used as a delivery device for the delivery of any type of therapeutic or diagnostic agent or modality or implantable device. For instance, therapeutics, such as pharmaceutical or biological agents, factors, proteins and cells; tissue repair or treatment polymers such as glues and adhesives; energy modalities, such as optical waveguides for delivery of laser energy, ultrasonic waveguides for the delivery of therapeutic ultrasound, microwave antennas and radio frequency (RF) conductors are just some of the examples of therapeutics contemplated for delivery through the catheter 22 due to its unique arrangement of the sensor coil 26 and lumen 24. Likewise, examples of suitable diagnostics for delivery through the catheter 22, include, but are not limited to: contrast agents, dyes, marking fluids or substances. Moreover, implantable devices such as miniature electronics, implantable sensors including biological diagnostic chips, pacing devices, prosthetics, etc. are also suitable with this arrangement.

System 20 further comprises radiator elements or coils 32, 34, 36, 38, 40, 42, 44, 46, and 48 (also known as generator coils). In one embodiment, the coils are wound in sets of three orthogonal and concentric coils forming radiators 56, 58, and 60, respectively. Preferably, the coils 32, 34, 36, 38, 40, 42, 44, 46, and 48 are each wound around a support member such as a spool. In this first embodiment, each radiator 56, 58 and 60 has three coils that are co-located. Accordingly, the coils of each radiator are concentric with each other and mutually orthogonal with each other. The concentric arrangement is accomplished by having each coil within a particular radiator shaped such that the coils with their respective support member each have a different diameter. For instance, by way of example with respect to radiator 56, coil 36 accommodates and receives coils 32 and 34 and coil 34 accommodates and receives coil 32. Thus, coil 36 (with its support member) has a diameter that is greater than the diameter of coil 34 (with its support member) wherein the diameter of coil 34 is greater than the diameter of coil 32 (with its support member). Likewise, this type of concentric arrangement is applied to all of the radiators 56, 58 and 60.

In this first embodiment, the radiators 56, 58 and 60 are fixedly mounted to define a plane or location pad 61. The radiators 56, 58 and 60 may be placed in any desired fixed arrangement such as an arrangement in the form of respective vertices of a substantially equilateral triangle having sides up to 1 meter in length. The radiator coils 32, 34, 36, 38, 40, 42, 44, 46 and 48 are connected by wires 62 to a radiator drive 64.

Generally, radiator drive 64 simultaneously energizes each of radiator coils 32, 34, 36, 38, 40, 42, 44, 46 and 48 through frequency multiplexing. Each of these coils generates a respective magnetic field (quasi-stationary field), which induces a voltage in sensing coil 26 which is used as a sensing signal. Accordingly, since each radiator coil 32, 34, 36, 38, 40, 42, 44, 46 and 48 generates a different magnetic field, the sensing signal that is generated at the sensing coil 26 is comprised of contributions from each of the radiator coils 32, 34, 36, 38, 40, 42, 44, 46 and 48. The sensing signal is then fed back to processor 25. The processor 25 then calculates the three position (x, y, z direction) and two orientation coordinates (pitch and yaw) (five degrees of freedom or 5 DOF) of the sensor coil 26 from the nine values of sensing signals. The method of calculation is described in detail later below. For instances where the sensing coil 26 has an asymmetrical shape, 6 DOF are calculated to include the roll orientation.

Figure 7:
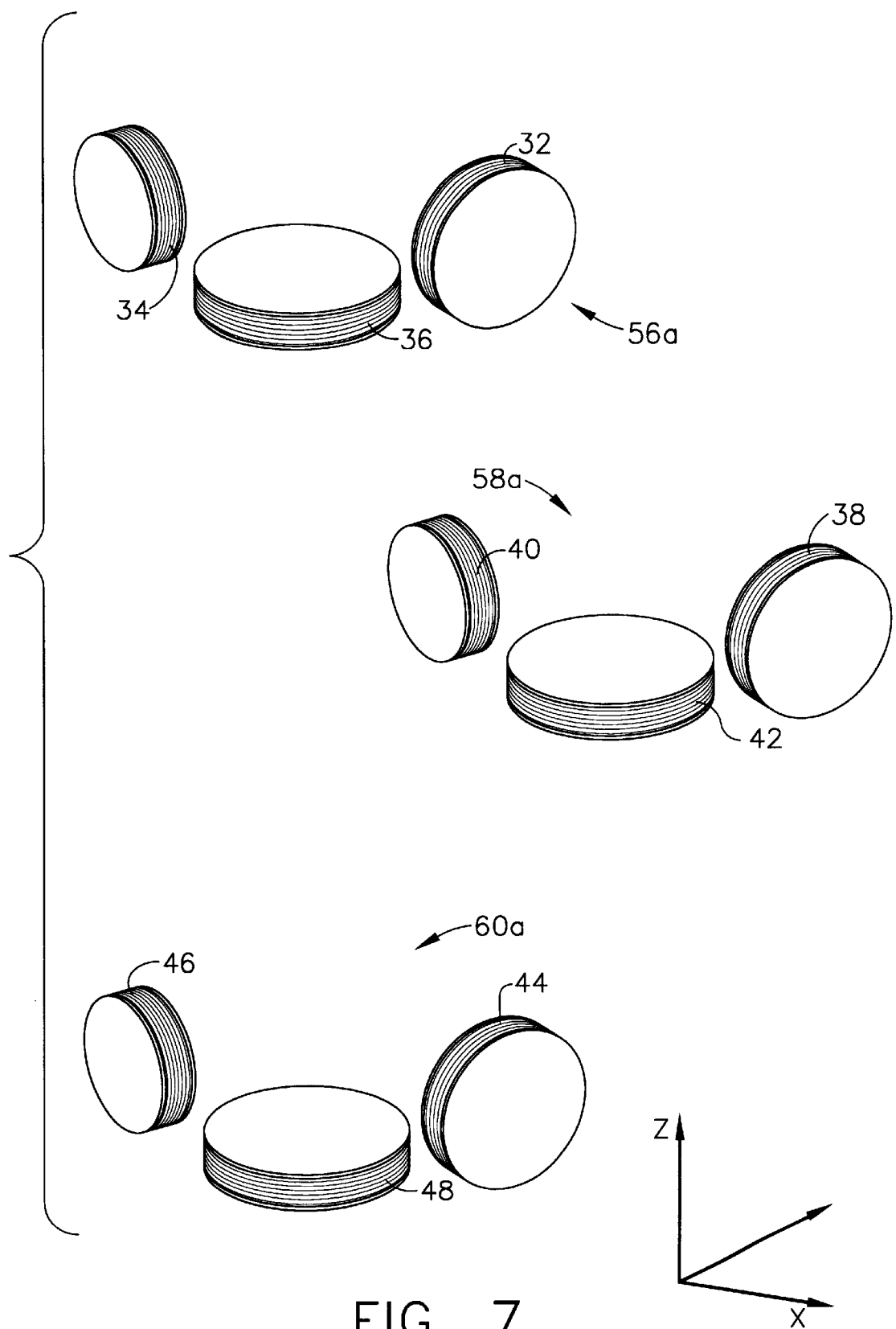
FIG. 7 is a schematic illustration of an alternative embodiment for a radiator arrangement according to the present invention having radiator coils that are not co-located but are mutually orthogonal to each other.

Additionally, there are other alternative radiator arrangement embodiments that are particularly useful with the present invention. As shown in FIG. 7, a second radiator arrangement includes radiators 56a, 58a and 60a having radiator coils 32, 34, 36, 38, 40, 42, 44, 46 and 48 respectively (same coils as mentioned above). The radiator coils 32, 34, 36, 38, 40, 42, 44, 46 and 48 are mutually orthogonal to each other within their respective radiator 56a, 58a and 60a. However, these radiator coils are not concentric and are not co-located. But rather, the radiators 56a, 58a and 60a comprise a spaced or nonco-located "triplet group" in which the distance between the coils of each nonco-located triplet grouping is no more than three to four times the size of the radiator coil diameter.

Figure 8:
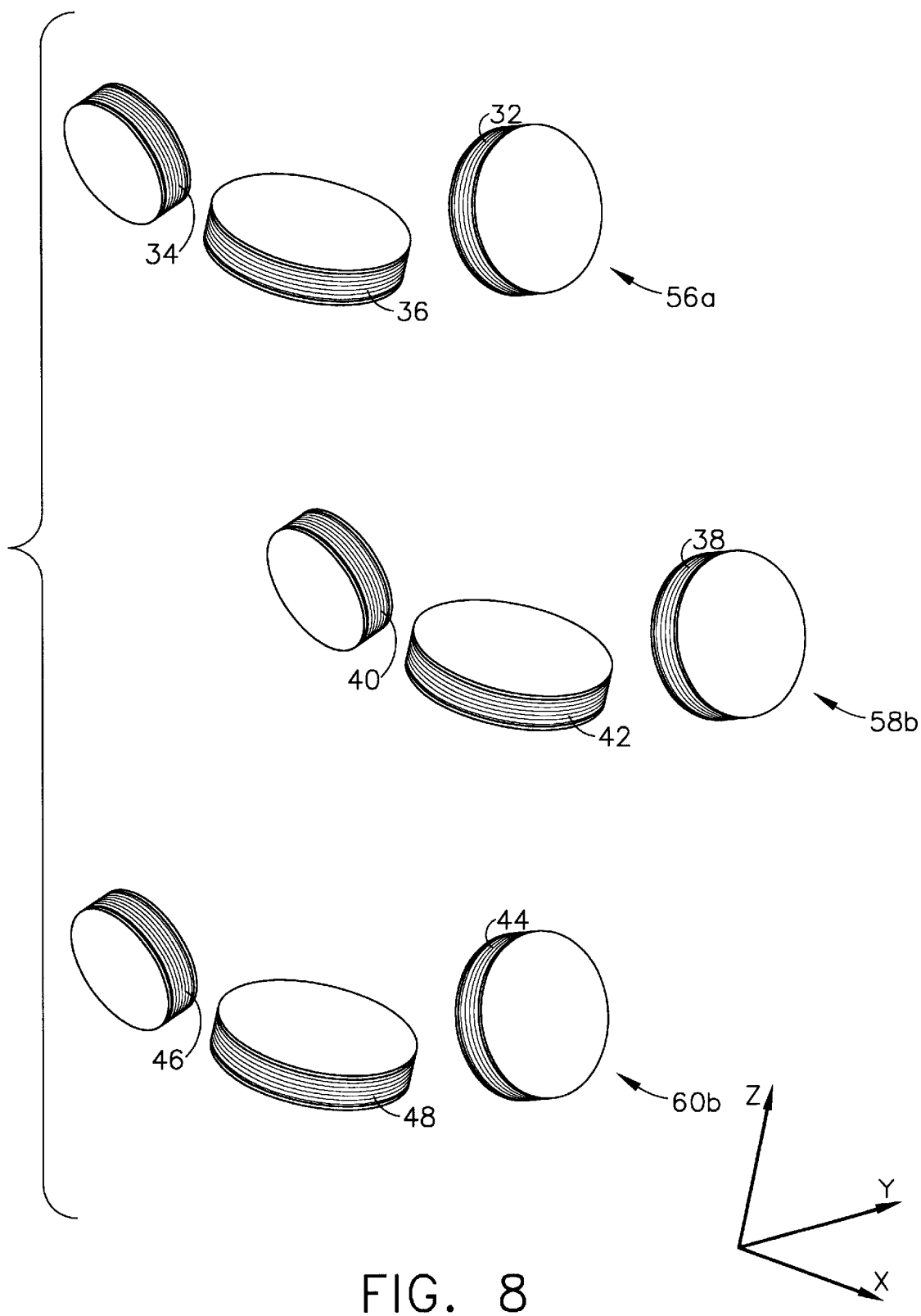
FIG. 8 is a schematic illustration of another alternative embodiment for a radiator arrangement according to the present invention having radiator coils that are not co-located and are not mutually orthogonal to each other.

A third radiator arrangement embodiment is shown in FIG. 8. In this embodiment, radiators 56b, 58b and 60b have radiator coils 32, 34, 36, 38, 40, 42, 44, 46 and 48 respectively that are not co-located, not concentric and are not mutually orthogonal to each other. The orientation of each coil is arbitrary with the only limitation being that one coil is not parallel to another coil of the same triplet grouping 56b, 58b and 60b.

Figure 9:
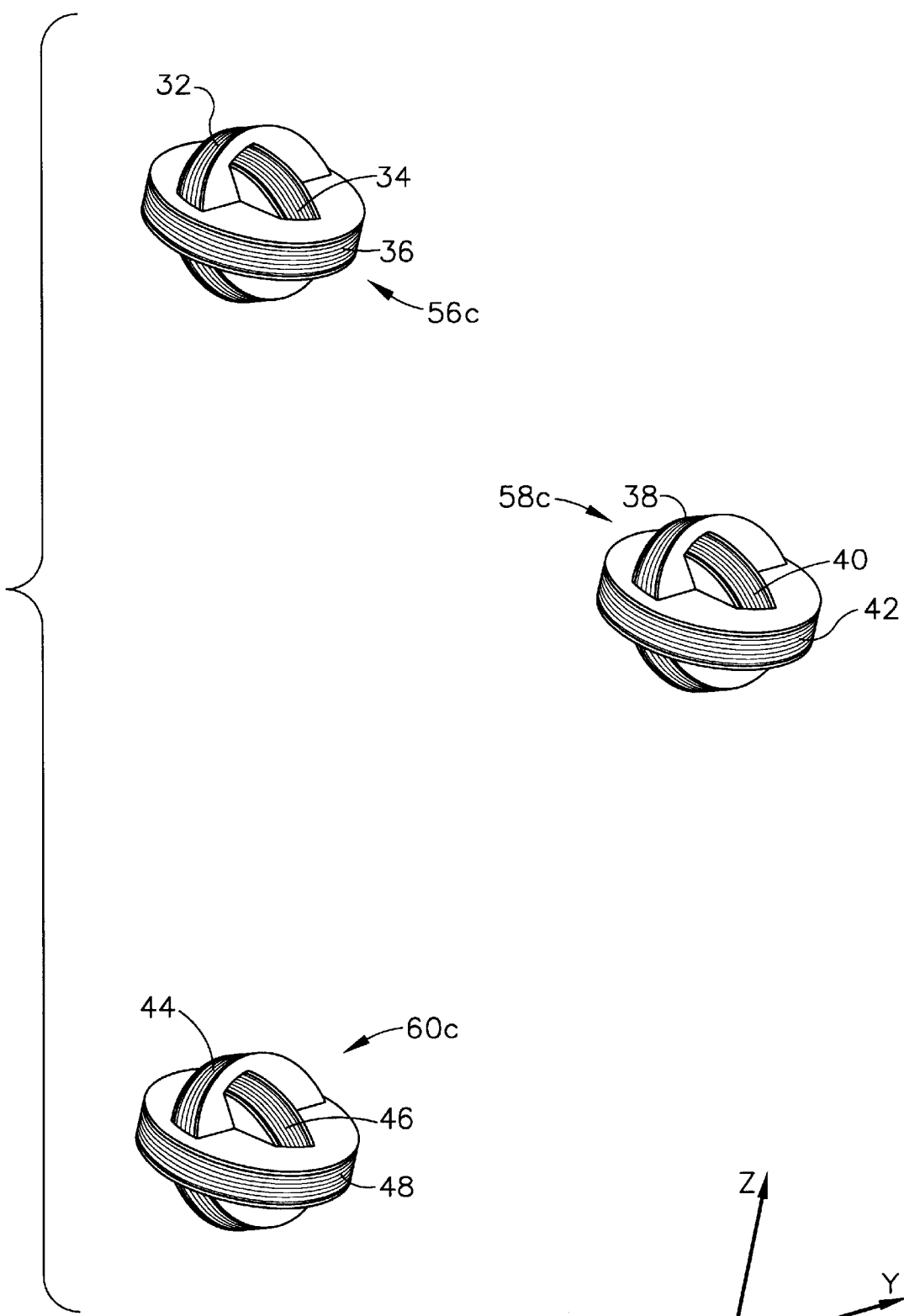
FIG. 9 is a schematic illustration of another alternative embodiment for a radiator arrangement according to the present invention having radiator coils that are co-located and but are not mutually orthogonal to each other.

FIG. 9 illustrates a fourth embodiment of a radiator arrangement in accordance with the present invention. In this embodiment, radiators 56c, 58c and 60c comprise a co-located arrangement for the radiator coils 32, 34, 36, 38, 40, 42, 44, 46 and 48 respectively wherein the coils of each radiator are concentric with respect to each other similar to the radiator embodiment of FIG. 2. However, the coils of each radiator 56c, 58c and 60c are are not orthogonal to each other. Again, the only limitation to the coil orientations is that one coil is not parallel to another coil in a particular radiator arrangement 56c, 58c and 60c.

Position and Orientation Method

Figure 3:
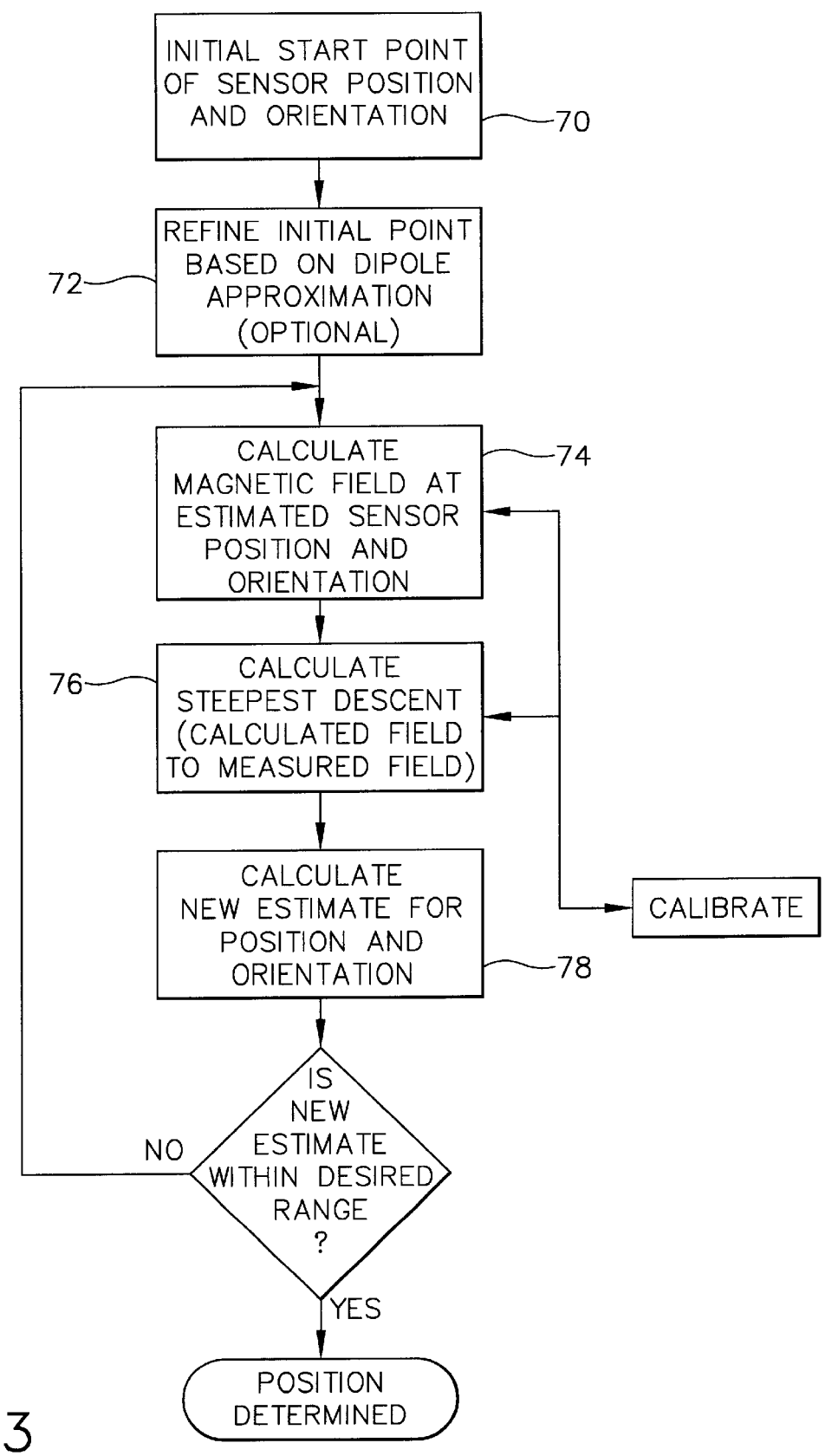
FIG. 3 is a schematic flow chart showing a method used to find position and orientation coordinates in accordance with a preferred embodiment of the present invention.

FIG. 3 is a schematic flow chart illustrating a method and associated algorithmic components for determining the coordinates of sensing coil 26, in accordance with a preferred embodiment of the present invention. The general method steps will be described below and the specific steps of the novel algorithm will be described in detail later in this disclosure. Signal processor 25 (FIGS. 1 and 2) determines three positions (X, Y, and Z) and two orientation (pitch and yaw) coordinates of sensing coil 26 by the method described herein. Prior to beginning any medical procedure, the system 20, through the signal processor 25, has been pre-programmed with a desired degree of accuracy achieved through calibration. This is a desired accuracy range which is usually ≦0.1 cm (the accuracy of the system). However, the incremental steps or iterations of the algorithm are stopped as soon as the change from a previous step is less than 0.001 cm. The last is necessary in order to get 1 mm accuracy). Additionally, for each system 20 that is manufactured, the generators 56, 58 and 60 through their generator coils 32, 34, 36, 38, 40, 42, 44, 46 and 48 respectively are uniquely calibrated by a novel calibration system and method which is described in greater detail later in this disclosure.

The system 20, such as the embodiment illustrated in FIG. 1, is located in a clinical setting, such as a surgical suite, and the locator pad 61 is positioned in a desired location. One preferred location is to position the locator pad 61 near the patient, for instance, beneath a non-metallic operating table (not shown). The system 20 is activated and the generator coils 32, 34, 36, 38, 40, 42, 44, 46 and 48 of the radiators 56, 58 and 60 are simultaneously energized wherein each coil radiates distinct electromagnetic fields, each having a distinct frequency. Accordingly, nine separate magnetic (quasi-stationary) fields are created. Due to the pre-fixed arrangement of the location pad 61, a predictable magnetic field volume (operating volume) covering approximately a 20 cm×20 cm×20 cm or (20 cm)$^3$ volume (based on the radiators 56, 58, and 60 being configured in location pad 61 in a triangular arrangement having sides of 40 cm×40 cm×37 cm) is projected at the patient which more than covers the areas desired for insertion and tracking of the catheter 22. It is important to note that these dimensions are just one of the illustrated examples of size contemplated by the present invention. Smaller and larger volumes are clearly contemplated by the present invention.

The catheter 22 is then placed in the patient and brought into the operating volume and the sensor coil 26 produces sensor signals indicative of the magnitude of the magnetic field at the sensor coil 26. These sensor signals are provided to the processor 25 through wire 28 wherein the magnitude of the magnetic field (measured field) is determined and stored in the processor 25.

As best shown in FIG. 3, at this point the signal processor 25 uses an arbitrary starting point (reflecting both position and orientation) and preferably utilizes a dipole approximation (an optional step) for one iteration in order to get from this arbitrary point to a starting position for the steepest descent. The arbitrary point is a pre-programmed starting point in the processor 25, for instance, usually a point chosen at the center of the mapping volume. Then, the program in the signal processor 25 moves directly into the calculation with no approximations. However, the convergence can be expedited (calculation time shortened) by using the dipole approximation as a first step thus bringing the solution closer to the actual position. From there, the full magnetic field with no approximations is utilized. Thus, the arbitrary starting point is used for the dipole approximation as well.

Once the initial position and orientation estimate is made with the dipole approximator 72, the processor 25 calculates the magnetic field at the estimated position and orientation using a magnetic field calculator 74. After this calculation, the steepest descent from the calculated magnetic field of the estimated sensor position and orientation to the measured magnetic field of the sensor coil 26 is calculated using a steepest descent calculator 76 which employs the Jacobian technique. It is important to note that the Jacobian is calculated for all nine radiator coils 32, 34, 36, 38, 40, 42, 44, 46 and 48 respectively by the steepest descent calculator 76. The magnetic field estimator 74 and the steepest descent calculator 76 use exact theoretical magnetic field expressions as well as pre-stored calibration data.

Based on this calculation, a resulting computation is made, which actually reflects a change (ΔX), indicating the steepest change in value between the new estimated position and orientation and the previous position and orientation (the actual position and orientation is not known until the end of the calculation). This result, $\vec{\Delta x}$, is added to the previous estimate of the sensor position and orientation to arrive at a new estimate of sensor position and orientation. Additionally, calibration information that has been pre-stored in the signal processor 25 in accordance with a novel calibration system and method of the present invention is also utilized (greater detail provided below). Accordingly, a predetermined calibration factor is used to adjust the Jacobian and the fields.

At this point, the new estimate of the position and orientation of the sensor coil 26 is compared to the predetermined desired accuracy range. If the new estimate of the position and orientation of the sensor coil 26 is not within this range, then the steps are repeated beginning with calculating the magnetic field at the new estimated position and orientation.

Additionally, for the alternative radiator arrangement embodiments illustrated in FIGS. 7–9, a global convergent technique is applied by a global converger 77 (FIG. 10) in order to arrive at a new estimate of position and orientation that is within the predetermined accuracy range. The specific algorithm is discussed in detail later below.

Position and Orientation Algorithm

Figure 4A:
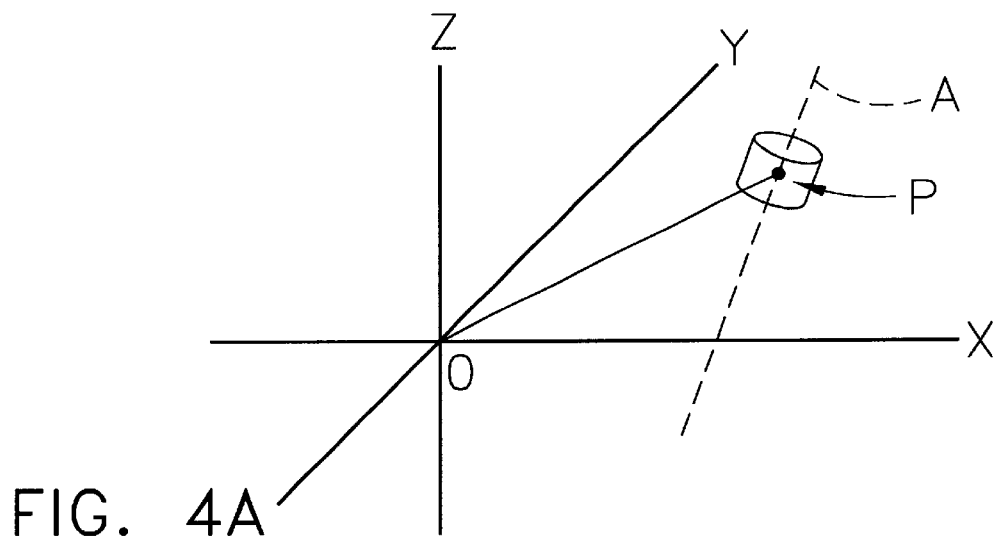
FIGS. 4A–4F are graphic illustrations of the method of FIG. 3.

In order to better understand the above-described method, the novel algorithm utilized by this method will now be specifically addressed according to each method step. For illustration purposes, the location and orientation of the sensor coil 26 is best described with respect to FIGS. 4A–4C. As shown in FIG. 4A, the center of the sensor coil 26 is positioned at point P. The axis of the sensor coil 26, which defines its orientation, is shown as dashed line A in FIG. 4A.

Figure 4B:
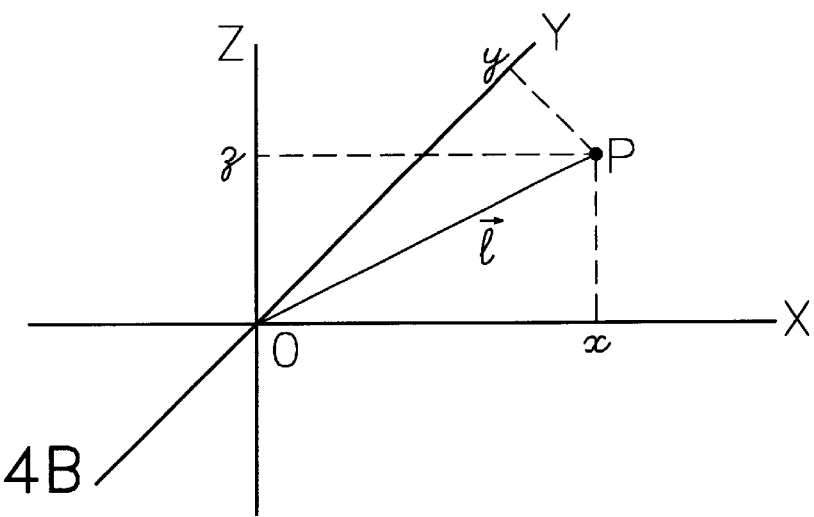
Figure 4C:
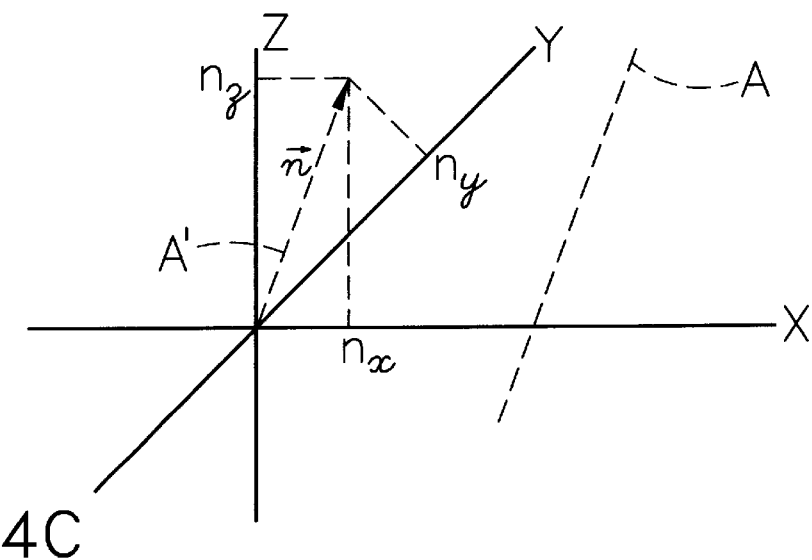

The position and orientation of the sensor $\vec{x}$ may be defined as follows:

$$\vec{x} = \{\vec{1}, \vec{n}\} \qquad (1)$$

wherein $\vec{1}$ equals the x, y and z coordinates of the position vector OP as shown in FIG. 4B. The vector $\vec{n}$, a measure of the sensor orientation, corresponds to the x, y and z coordinates, $n_x$, $n_y$, and $n_z$, respectively, of A' (see FIG. 4C), an orientation vector which is a parallel translation to the origin of sensor axis orientation vector A.

Figure 4D:
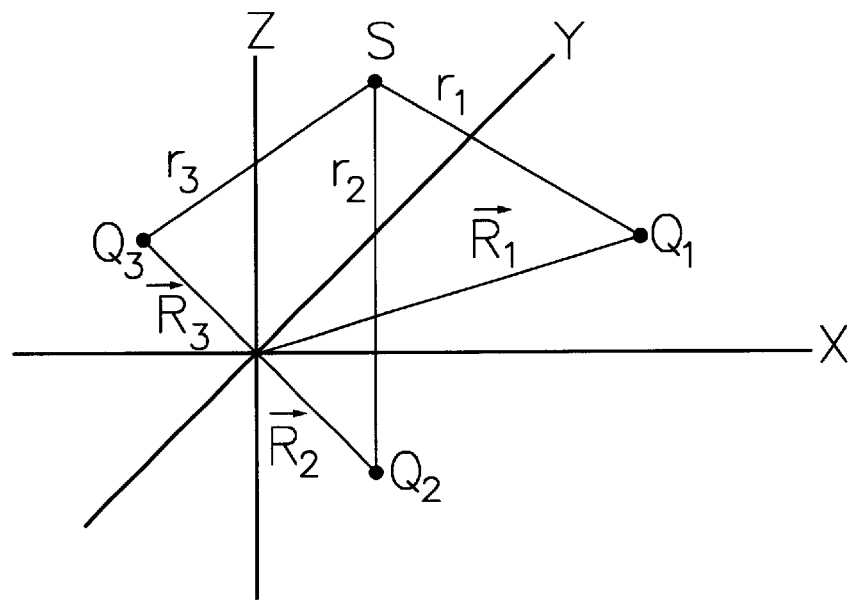

A partial schematic drawing of the system 20 of the invention is depicted in FIG. 4D in which $Q_1$, $Q_2$ and $Q_3$ are the three radiators 56, 58 and 60 respectively. Each of these radiators 56, 58 and 60 comprises three coils (32, 34, 36, 38, 40, 42, 44, 46 and 48 respectively). For ease of illustration, radiator $Q_1$ comprises radiator coils one, two and three (32, 34 and 36); radiator $Q_2$ comprises coils four, five and six (38, 40 and 42); and radiator $Q_3$ comprises coils seven, eight and nine (44, 46 and 48).

With this arrangement, through the sensor coil 26, measurements of the fields at the sensor coil 26 due to each radiator coil 32, 34, 36, 38, 40, 42, 44, 46 and 48 is provided to the processor 25 for use with detailed steps below.

Step (a): Determine the initial estimate of sensor position and orientation using the initial position and orientation estimator 70.

For the initial estimate of sensor position and orientation, we assume an arbitrary position of the sensor coil 26 as follows:

$$\vec{x}_0 = \{\vec{1}_0, \vec{n}_0\} \qquad (2)$$

Figure 4E:
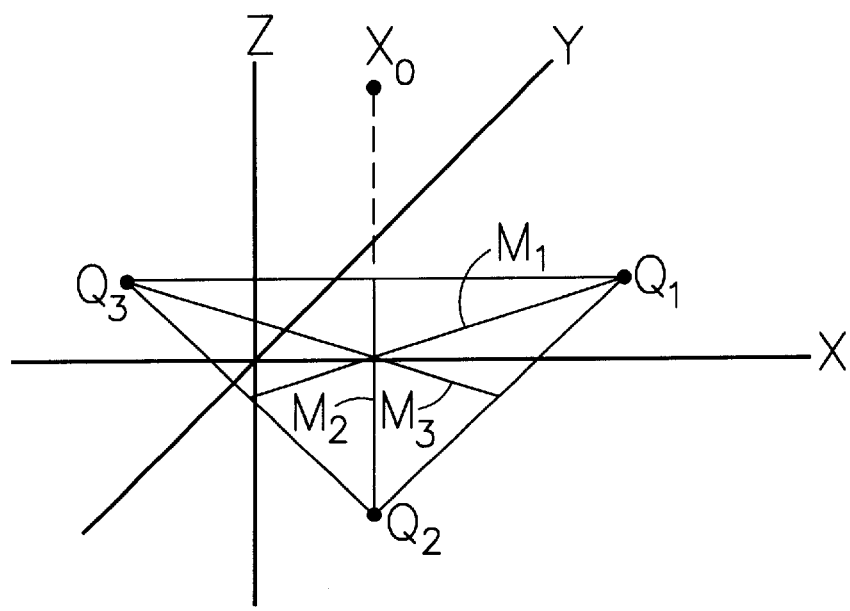

For convenience, $\vec{x}_0$ may be arbitrarily chosen so as to be approximately in the center of the system location volume. For example, the three radiators $Q_1$, $Q_2$ and $Q_3$ may be viewed as being placed at the vertices of a triangle (FIG. 4E). The sides of the triangle may be bisected by medians $M_1$, $M_2$ and $M_3$. The initial estimate of the three-dimensional sensor position $\vec{1}_0$ may be chosen to be at the intersection of the medians of the radiators, at a distance, 20 cm for example, above the plane formed by the radiators. Likewise, for convenience, $\vec{n}_0$ may be chosen to be a positive unit vector parallel to the z axis.

Optional Step (b): Refinement of the estimated sensor position and orientation based on the dipole approximation using the dipole approximator 72.

The initial estimate of the sensor position and orientation may be refined using the dipole approximator 72 based on the dipole approximation, as described below:

As shown in FIG. 4D, we may define the vectors $\vec{R}_1$, $\vec{R}_2$ and $\vec{R}_3$ as the position vectors from the origin to the radiator centers for radiators $Q_1$, $Q_2$ and $Q_3$, respectively. S defines the coordinate of the sensor coil 26. For each of the radiators, we may define a relationship $a_j$ (j=1 to 3) as follows: $\vec{P}_j = \vec{R}_j - \vec{X}_0$, where $\vec{X}_0$ is an Initial position:

$$a_1 = \frac{\vec{P}_1 \cdot \vec{R}_1}{|\vec{P}_1| \cdot |\vec{R}_1|} \quad (3)$$

$$a_2 = \frac{\vec{P}_2 \cdot \vec{R}_2}{|\vec{P}_2| \cdot |\vec{R}_2|} \quad (4)$$

$$a_3 = \frac{\vec{P}_3 \cdot \vec{R}_3}{|\vec{P}_3| \cdot |\vec{R}_3|} \quad (5)$$

We may define $f_i$ for i=1 to 9 as the measured field values at the sensor S of the fields attributed to coils numbers one (1) through nine (9). The magnetic field values for each coil are measured according to the known techniques as outlined in commonly assigned PCT patent application publication WO 96/05768 which is incorporated herein by reference.

We may also define $m_j$ for j=1 to 3 as the sum of the squares of the measured fields at the sensor due to the coils comprising each of the radiators. Thus, for the system shown in FIG. 2 and FIG. 4D, we have three equations in m as follows:

$$m_1 = f_1^2 + f_2^2 + f_3^2,$$

$$m_2 = f_4^2 + f_5^2 + f_6^2, \text{ and}$$

$$m_3 = f_7^2 + f_8^2 + f_9^2.$$

A sensor at points far removed from the radiator coils (distance from point to the radiator>radiator coil radius) will experience magnetic fields that are said to be dipolar in character (see for example J. D. Jackson in Classical Electrodynamics, second edition, John Wiley & Sons, New York, 1975, page 178, which is incorporated herein by reference). Under these conditions, as shown in U.S. Pat. No. 5,913,820 which is incorporated herein in its entirety by reference, for the case of three radiators $Q_1$, $Q_2$ and $Q_3$, each radiator composed of three concentric and orthogonal radiator coils, the distance from the sensor to each of the radiators may be approximated in terms of the above-defined and calculated values of a and m by the following equations:

$$r_1 = \left[ \frac{\sqrt{1 + 3a_1^2}}{m_1} \right]^{\frac{1}{3}}$$

$$r_2 = \left[ \frac{\sqrt{1 + 3a_2^2}}{m_2} \right]^{\frac{1}{3}}$$

$$r_3 = \left[ \frac{\sqrt{1 + 3a_3^2}}{m_3} \right]^{\frac{1}{3}}$$

wherein $r_1$, $r_2$ and $r_3$ are the distances from the sensor to the center of radiators $Q_1$, $Q_2$ and $Q_3$, respectively. We may use the three distances $r_1$, $r_2$ and $r_3$ to triangulate to an approximate sensor location $\vec{1}(x,y,z)$. Each of the three distances $r_1$, $r_2$ and $r_3$ may be thought of as radii of spheres about each of the radiators. The triangulation process solves for the point of intersection of these three spheres, which results in an approximate sensor location as described by $\vec{1}(x,y,z)$ (see FIGS. 4B and 4F).

Knowing the characteristics of each of the radiator coils (number of windings, coil diameter, etc.) and the current passing through these coils, we may calculate $\vec{H}(\vec{1})$, a [9, 3] matrix describing the theoretical field in each of the x, y and z directions attributed to each of the nine radiator coils at the approximate sensor location defined by vector $\vec{1}$.

Figure 4F:
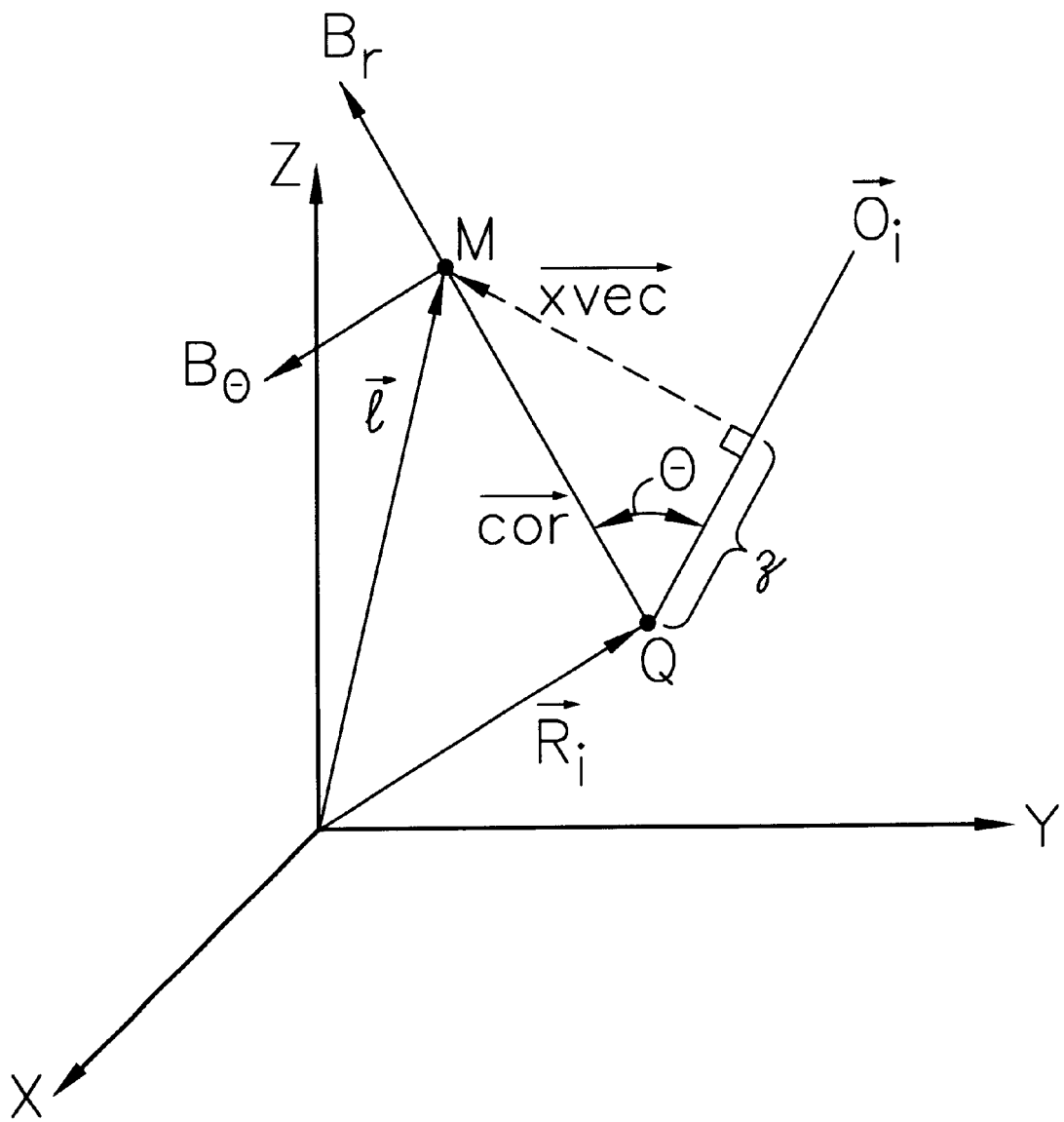

FIG. 4F shows a single loop radiator coil centered at Q and having a unit orientation vector $\vec{O}_i$. The coil is centered a distance $\vec{R}_i$ from the origin of the three-dimensional frame of reference. The vector $\vec{1}$ connects the origin with point M, the approximate sensor location from the triangulation as discussed above. The theoretical field at M due to radiator coil i may be found as follows:

We may define the vector $\vec{cor}$ such that: $\vec{cor} = \vec{1} - \vec{R}_i$.

The vector $\vec{cor}$ is of magnitude corresponding to the distance between the coil center, point Q, and point M.

We may also define the scalar quantity z as the dot product of $\vec{O}_i$, a vector describing the radiator coil axis, and the vector $\vec{cor}$: $z = \vec{O}_i \cdot \vec{cor}$.

The quantity z, as shown in FIG. 4F, is equal to the projection of $\vec{cor}$ on $\vec{O}_i$.

We may define the scalar quantity absr as the absolute value of the vector $\vec{cor}$: $absr = \|\vec{cor}\|$.

The scalar absr is equal to the distance between the coil center and point M.

We may find $B_r$ and $B_\theta$, vector components of the magnetic flux density at the point M resolved along axes parallel and perpendicular, respectively, to the line connecting point M and the coil as outlined in PCT patent application publication WO 96/05768.

We may also define the quantities $\vec{xvec}$ and xnor as follows:

$$\vec{xvec} = \vec{cor} - (z \cdot \vec{O}_i)$$

$$xnor = \|\vec{xvec}\|.$$

It follows then from these relationships, as illustrated in FIG. 4F that $$\sin\theta = \frac{xnor}{absr}$$
$$\cos\theta = \frac{z}{absr}.$$

We may determine the magnetic field at location M in the frame of reference of the radiator coil ($\vec{xvec}$ and $O_i$) by solving the following rotation matrix:

$$\vec{G} = \begin{pmatrix} \sin\theta & \cos\theta \\ \cos\theta & -\sin\theta \end{pmatrix} \begin{pmatrix} B_r \\ B_\theta \end{pmatrix} = \begin{pmatrix} G_{xvec} \\ G_{O_i} \end{pmatrix}.$$

The field $\vec{F}_0$ at M in the frame of reference of the x, y, z coordinate system of FIG. 4F due to a radiator coil having a single turn is now given by the following equation:

$$\vec{F}_o = \left(\frac{\vec{xvec}}{xnor}\right) \cdot G_{xvec} + \vec{O}_i \cdot G_{O_i}.$$

The calculated magnetic field $\vec{F}_i$ at M due to coil i having more than one turn is given by the following equation:

$$\vec{F}_i = \vec{F}_0 \cdot (\text{effective number of turns of the coil}).$$

The effective number of turns of a coil may not be equal to the actual number of turns due to inhomogeneities in the coil, caused, for example, by turns of different radii or by nonparallel turns. The effective number of turns of the coil may be determined by calibration of the coil, for example, by the method disclosed in PCT patent application publication WO 97/42517, the disclosure of which is incorporated herein in its entirety by reference.

The calculation above provides the magnitude of the magnetic field at M due to coil i in each of the x, y and z directions. This calculation is repeated for each of the coils to provide the data for the matrix $\vec{H}(\vec{l})$ as defined above.

We may now define a quantity $\vec{h}(\vec{x})$, the calculated field of a sensor at M corrected for sensor orientation $\vec{n}$ as follows:

$$\vec{h}(\vec{x}) = \vec{H}(\vec{l}) \cdot \vec{n}.$$

Making the approximation that the sensor is actually located at the location value given by vector $\vec{l}$, we may then substitute $\vec{f}$, the actual measured value of the fields at the sensor for $\vec{h}(\vec{x})$ in the above equation, affording $$\vec{f} \approx \vec{H} \cdot \vec{n}.$$

Rearranging this equation affords the following equation which provides a first approximate calculation of the sensor orientation vector $\vec{n}$ as follows:

$$\vec{n} = \vec{H}^{-1} \cdot \vec{f}.$$

Step (c): Calculate the magnetic field at the estimated sensor position and orientation using magnetic field calculator 74.

We recall from the Equation above that $$\vec{h}(\vec{x}) = \vec{H}(\vec{l}) \cdot \vec{n}.$$

Having previously calculated $\vec{H}(\vec{l})$ at approximate sensor location M denoted by vector $\vec{l}$, and having calculated an approximate sensor orientation $\vec{n}$, we may now calculate $\vec{h}(\vec{x})$, the calculated field at position and orientation $\vec{x} = \{\vec{l}, \vec{n}\}$ using the Equation above. The vector $\vec{h}(\vec{x})$ is the orientation-corrected magnetic field due to each of the nine radiator coils at a sensor at approximate position and orientation $\vec{x} = \{\vec{l}, \vec{n}\}$, and, for the above-described system, is of the form of a [9, 1] matrix.

Step (d): Calculate the steepest descent (the Jacobian) from the calculated magnetic field at the estimated sensor position and orientation to the measured magnetic field at the sensor using the steepest descent calculator 76.

We may calculate the Jacobian at $\vec{x} = \{\vec{l}, \vec{n}\}$ as follows:

$$\vec{J}_{ij} = \frac{\partial(H(\vec{l}) \cdot \vec{n})}{\partial \vec{x}_j} = \frac{\partial \vec{h}(\vec{x})_i}{\partial \vec{x}_j}.$$

The Jacobian, $J_{ij}$, is the change in the calculated field $\vec{h}(\vec{x})$ at calculated location and orientation $\vec{x} = \{\vec{l}, \vec{n}\}$ for each of the nine radiator coils (i=1 to 9), with respect to each of the six position and orientation variables (j=1 to 6). The Jacobian is a 9 by 6 matrix having 9 rows and 6 columns. Each element in the Jacobian matrix is calculated by calculating the field due to each coil i at the position $\vec{x}$. We then increment each of the six position variables by a Δ and then recalculate the field. The change in the field due to coil i with respect to each of the six position variables represents the six entries in the Jacobian matrix for coil i. The process is repeated for each of the nine coils.

In practice, it is quite computationally intensive to do all these calculations. Alternatively and preferably, values for each of the entries in the Jacobian may be calculated once and stored in a lookup table. Individual entries may then be obtained by interpolation between lookup table values wherein the increments in $\vec{x}$ are predetermined in the lookup table.

We may define the matrix L, a 6 by 9 matrix, as follows:

$$\vec{L} = [J(J^T \cdot J)^{-1}]^T.$$

Matrix L is a mean least squares inversion of the Jacobian.

We may compute $\vec{b}$, the difference between the actual field at the sensor and the calculated field at the calculated sensor position and orientation as follows:

$$\vec{b} = \vec{f} - \vec{h}.$$

We recall Equation that:

$$\vec{h}(\vec{x}) = \vec{H}(\vec{l}) \cdot \vec{n}.$$

At the actual sensor location, the actual measured field would be equal to the calculated field, which gives rise to the following equation:

$$\vec{h}(\vec{x}) = \vec{f}(\vec{x}).$$

At an approximate sensor location, the field at the approximate location, $\vec{H}(\vec{x})$, can be related to the measured field at the actual sensor location $\vec{f}$ as follows:

$$\vec{f} = \vec{h}(\vec{x}_{n-1}) + \frac{\partial H}{\partial x} \cdot \vec{\Delta x}$$

Recall that, $$\vec{b} = \vec{f} - \vec{h}(\vec{x}_{n-1}).$$

Since, $$\vec{L}J = I$$

$$\left\{ J \equiv \frac{\partial H}{\partial x}, I \equiv \begin{pmatrix} 1 & 0 & 0 & 0 & 0 & 0 \\ 0 & 1 & 0 & 0 & 0 & 0 \\ 0 & 0 & 1 & 0 & 0 & 0 \\ 0 & 0 & 0 & 1 & 0 & 0 \\ 0 & 0 & 0 & 0 & 1 & 0 \\ 0 & 0 & 0 & 0 & 0 & 1 \end{pmatrix} \right\}$$

Thus, we wish to calculate a change ($\Delta x$) in the six-dimensional position and orientation variable $\vec{x}$, which will cause the measured field to approach, and, ultimately, to equal the computed field at the calculated position and orientation of the sensor. From the parameters and equations defined above, that value of $\Delta x$ which most steeply changes the calculated field at the calculated position and orientation in the direction of the measured field is given as follows:

$$\vec{\Delta x} = \vec{L} \cdot \vec{b}.$$

The vector $\vec{\Delta x}$ represents the value that is added to each of the six position and orientation coordinates of the estimated sensor location and orientation to arrive at a new estimate of the sensor position and orientation for which the calculated field is closer to the measured field.

Step (e): Calculate new estimate for sensor position and orientation using the new position and orientation estimator 78.

Having computed a value of $\vec{\Delta x}$, we may add this value of $\vec{\Delta x}$ to the previous estimate of the sensor position and orientation to arrive at a new estimate of sensor position and orientation, as follows:

$$\vec{x}_n = \vec{x}_{n-1} + \vec{\Delta x}.$$

Additionally, pre-stored calibration information (a calibration factor) according to a plurality of points within the operating volume is introduced at the magnetic field calculator 74 and the steepest descent/Jacobian calculator 76 in order to arrive at the new value/estimate of the position and orientation of the sensor at the new estimate calculator 78. Accordingly, the calibration data is used with the process recited above since it is related to the calculation of the magnetic fields at the sensor coil 26 and the Jacobian. This calibration method is described in greater detail below.

Step (f): Determine whether the new estimate of position and orientation is within the desired measurement accuracy, e.g. $\leq 0.1$ cm (the accuracy of the system). However, the incremental steps of the algorithm are stopped as soon as the change from a previous step is less than 0.001 cm as described above which is necessary in order to get better than 1 mm accuracy for the system.

One or more criteria may be specified to establish the required accuracy of the newly estimated sensor position and orientation values. One criterion examines the absolute value of $\vec{\Delta x}$, the position and orientation correction. If $|\vec{\Delta x}|$ is less than a particular threshold value, it may be assumed that the position and orientation has been calculated to the desired accuracy. For example, a value of $|\vec{\Delta x}| \leq 10^{-4}$ cm (which results in an accuracy of more than 1 mm) is believed to meet the required accuracy criteria for sensors used in most biomedical applications.

The above-described method of determining the sensor position and orientation involves calculation of the field $\vec{h}(\vec{x})$ at the estimated sensor position and location $\vec{x} = \{\vec{1}, \vec{n}\}$. We may define the quantity $\Delta f$ as follows:

$$\Delta f = \frac{|\vec{h} - \vec{f}|}{|\vec{f}|}.$$

The value of $\Delta f$ is another criterion that may be used to determine whether the sensor position and orientation have been found to the desired accuracy. For example, a value of $\Delta f \leq 10^{-4}$ (which results in an accuracy of more than 1 mm) has been found to be sufficiently accurate for most biomedical applications.

Preferably both of these criteria are used to determine that position and orientation values have been determined with the required accuracy.

Step (g): Iterate field calculations (steps (c)–(e)) at newly estimated sensor position and orientation to refine position and orientation estimate.

The procedure described hereinabove in steps (c) through (e) is iterated if the estimated position and orientation values do not meet one or both of the required accuracy criteria. Specifically, the newly estimated sensor position and orientation values from step (e) are used in step (c) to recalculate a magnetic field at the new estimated sensor position and orientation. The thus-calculated field value is used in step (d) to refine the steepest descent calculation. The refined steepest descent is used to determine a new estimate for the sensor position and orientation. One fail-safe mechanism utilized by the present invention is to limit the iteration number to a maximum number, for instance, to ten (10) iterations, so that if the algorithm does not converge for some reason, for example, due to the sensor coil 26 being out of range, or a hardware problem, then the system 20 would not go into an infinite loop. The maximum iteration number or iteration number limit is also stored in the signal processor 25.

Figure 10:
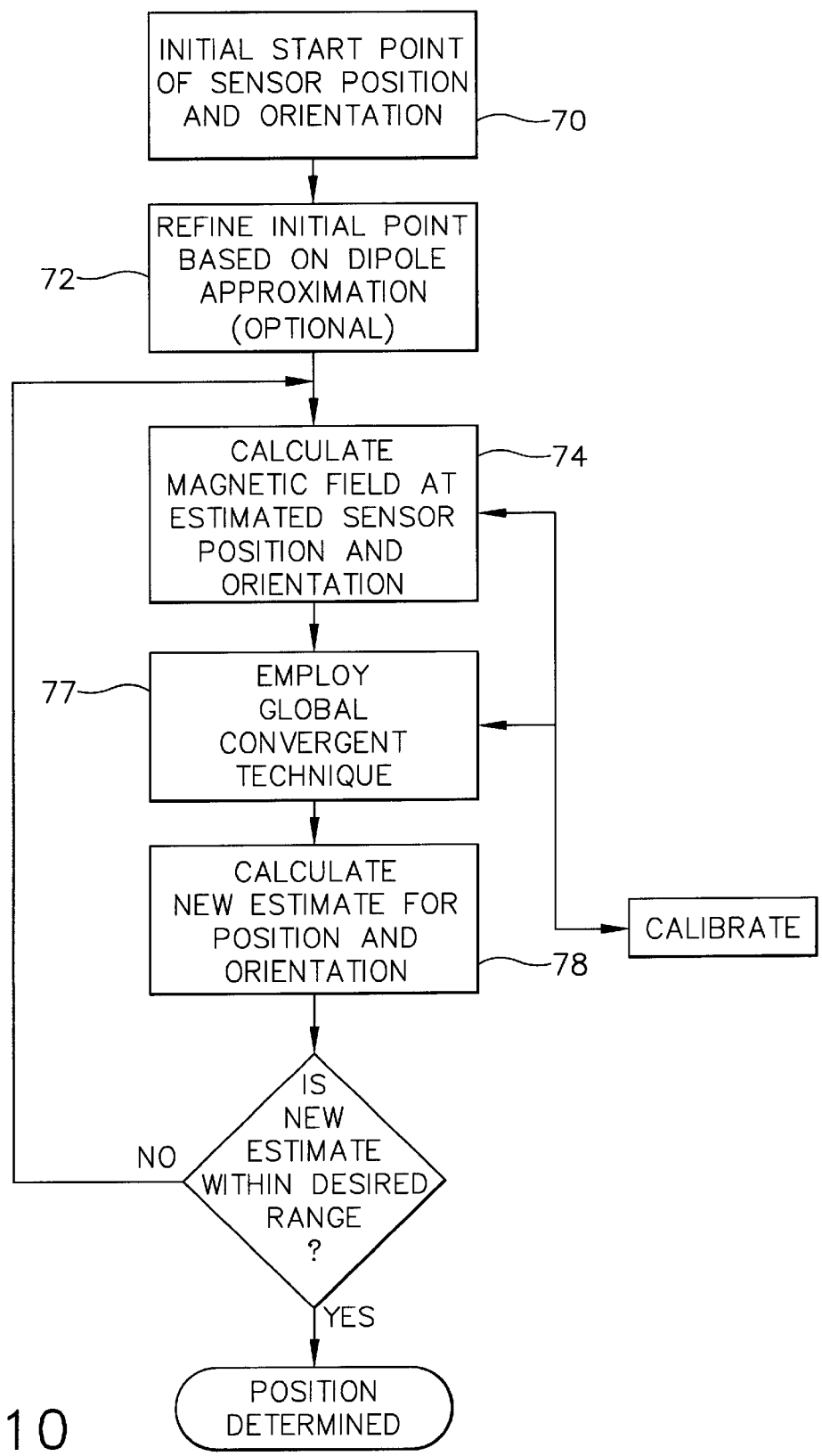
FIG. 10 is a schematic flow chart showing a method used to find position and orientation coordinates with the radiator arrangements of FIGS. 7–9 in accordance with another preferred embodiment of the present invention.

A modification to the algorithm described above is employed for the alternative radiator arrangements illustrated in FIGS. 7–9. This modified algorithm is based on a "Global Convergent" method as outlined in Numerical Recipes (ISBN 052143108 pp.383) which is incorporated by reference herein. By utilizing a global convergent technique (as shown in FIG. 10), a more efficient convergence of the arbitrary starting point to the actual sensor position and orientation is achieved. Accordingly, the technique according to the present invention provides for a new correction to the current position $\Delta X$ (as a replacement for the Jacobian step performed by the steepest descent calculator 76 of FIG.

3). This novel global convergence method comprises the following steps:

First, determine the direction of $\Delta X$ by the formula:

$$\Delta X/|\Delta X|.$$

Second, find the minimum value of the change in the Field $\Delta F$ ($\Delta F$ min.) along this direction. This position is determined by:

$$\Delta X' = C^* \Delta X (\text{where } 0 < C < 1).$$

Third, update the sensor position according to:

$$X = X + \Delta X'.$$

It is important to note that $\Delta X$ correction may not minimize the function $\Delta F$ if the estimated sensor position is too far from the actual position value. However, the direction of $\Delta X$ is the desired focus at this step. Thus, $\Delta F$ min. is determined by incrementing along the direction of $\Delta X$. Accordingly, this value will be anywhere between 0 and $\Delta X$.

If the global convergent algorithm does not converge (within a predefined number of iterations) from a certain starting position, a different starting point may be selected. For instance, a point adjacent to the initial starting point may be utilized in the global convergent algorithm above until there is convergence.

One helpful technique is to divide the operating volume or working space into subvolumes of 5 cm×5 cm×5 cm or (5 cm)³ so that there are a total of sixty-four trials to ensure convergence in any case. Accordingly, this procedure may be performed only once. Thus, after finding the first point, the result from the convergent technique is then used as an approximation for the algorithm.

To summarize then, the method of the invention consists of the following steps:

Step (a): Estimate an initial sensor position and orientation;

Optional Step (b): Refine the estimated sensor position and orientation based on the dipole approximation;

Step (c): Calculate the magnetic field at the estimated sensor position and orientation;

Step (d): Calculate the steepest descent from the calculated field at the estimated sensor position and orientation to the measured field at the sensor;

Step (e): Calculate a new estimate for sensor position and orientation which includes utilizing predetermined and stored calibration information stored in signal processor 25 in conjunction with steps (c) and (d);

Step (f): Determine whether the newly estimated position and orientation are within the desired accuracy of the measurement; and Step (g): Iterate the calculations (steps (c)–(e)), up to the pre-stored maximum iteration number, i.e. the iteration number limit, at the newly estimated sensor position and orientation to refine the position and orientation estimate to the required accuracy (also predetermined and stored in signal processor 25).

Alternatively, Step (d) above is replaced by the global convergent technique described above (FIG. 10) (for the radiator arrangements shown in FIGS. 7–9).

In practice, the method of the invention is applied to the sequential calculation of multiple number of sensors positions and orientations at a plurality of points in space. For the calculation of successive points that are closely spaced in time, it may be assumed that the sensor has not moved significantly since the previously determined values. Accordingly, a good value for the initial estimate of position and orientation for the $n^{th}$ position and orientation will be the values determined at the $n-1^{st}$ position and orientation.

Calibration System

Figure 5:
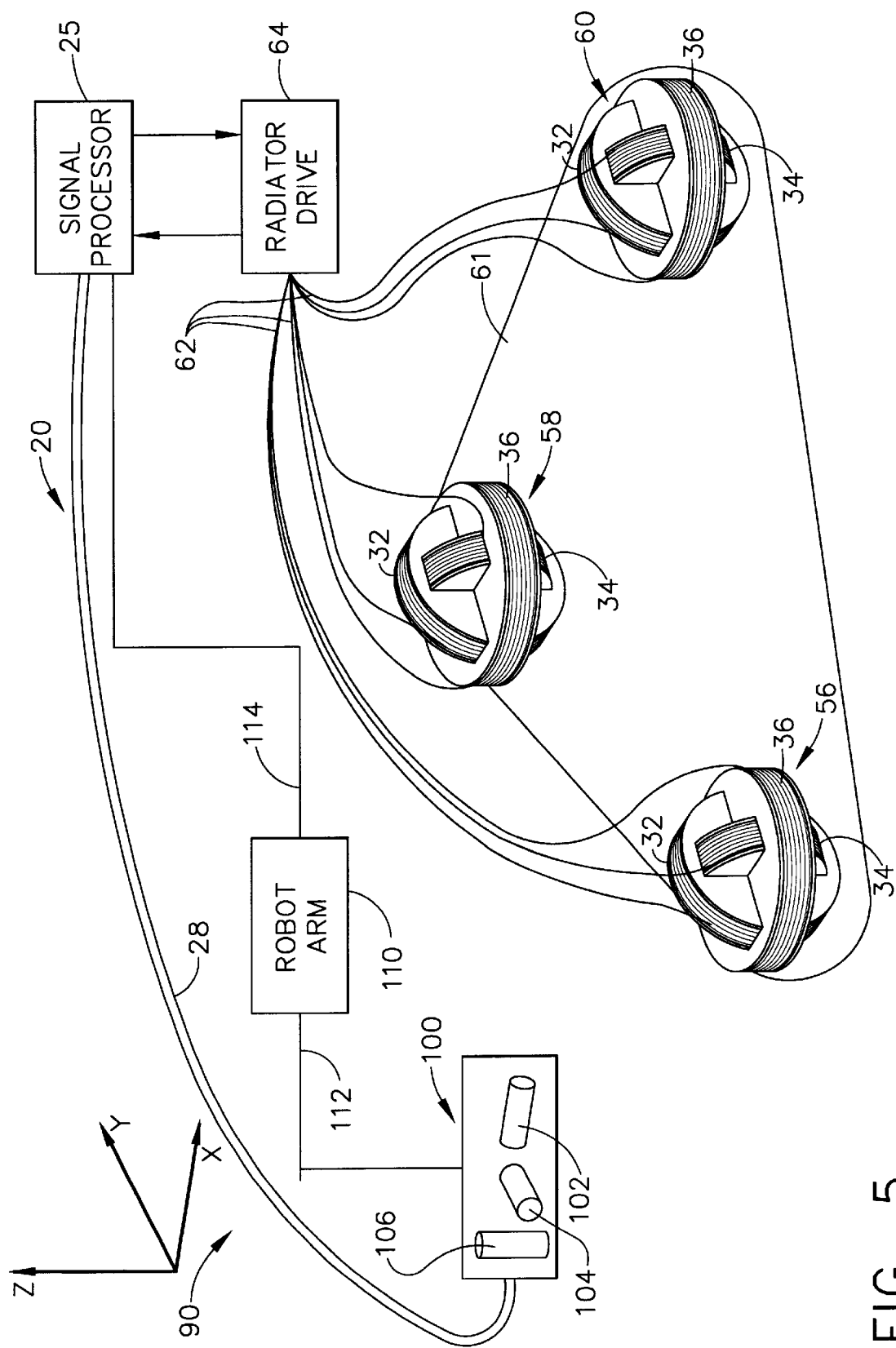
FIG. 5 is a schematic illustration of a calibration system according to the present invention.

A calibration system 90 according to the present invention is operably connected to the position and orientation sensing system 20 (FIGS. 1 and 2). The calibration system 90 is directed at providing calibration data that is pre-stored in the signal processor 25 which is used in performing an accurate determination of the sensor coil 26 (FIG. 2) position and orientation when introduced into the operating volume. As shown in FIG. 5, the calibration system 90 includes primary components of the position and orientation system 20 including the signal processor 25, the radiator drive 64, the location pad 61 and radiator or generator coils 32, 34, 36, 38, 40, 42, 44, 46 and 48 wound around spools forming radiators or generators 56, 58 and 60 respectively along with the respective wires 62.

The calibration system 90 further includes a test position sensor 100 having three sensor coils 102, 104 and 106 which are oriented in the X, Y and Z coordinate planes (coordinate axes) respectively as depicted. The pitch distances between the coils in the sensor 100 is 1–0.02 cm. The test position sensor 100 is operably connected to the signal processor 25 by wire 28 for processing sensor signals provided by the test position sensor 100. Additionally, the test position sensor 100 is operably connected to a positioning device such as a robot arm 110 by wire 112. The robot arm 110 is operably connected to the signal processor 25 by wire 114. The processor 25 has predetermined test positions according to the three coordinate system, e.g. X, Y, Z coordinate axes. Preferably, approximately one hundred and fifty (150) test positions are predetermined and stored in the processor 25. These test positions closely align with the operating volume produced by the generators 56, 58 and 60 when energized. Since the processor 25 is programmed with each of these test positions, the robot arm 110 can be accurately guided and positioned at each test position. This method will become much clearer when described in greater detail below.

Calibration Method Including Algorithm

In general, in the calibration method according to the present invention, the theoretical fields of the location pad 61 (FIG. 5) are adapted to the measured field of a specific position and orientation system 20. Accordingly, each system 20 is customized with its own calibration data which is used during the location calculations when determining the position and orientation of a sensor coil 26 (FIGS. 1 and 2) as mentioned above and depicted in the schematic flow chart of FIG. 3. Commonly assigned pending U.S. patent application Ser. No. 09/180,244, entitled Radiator Calibration, also addresses techniques for calibrating magnetic field generators or radiator coils and is incorporated by reference herein.

Figure 6:
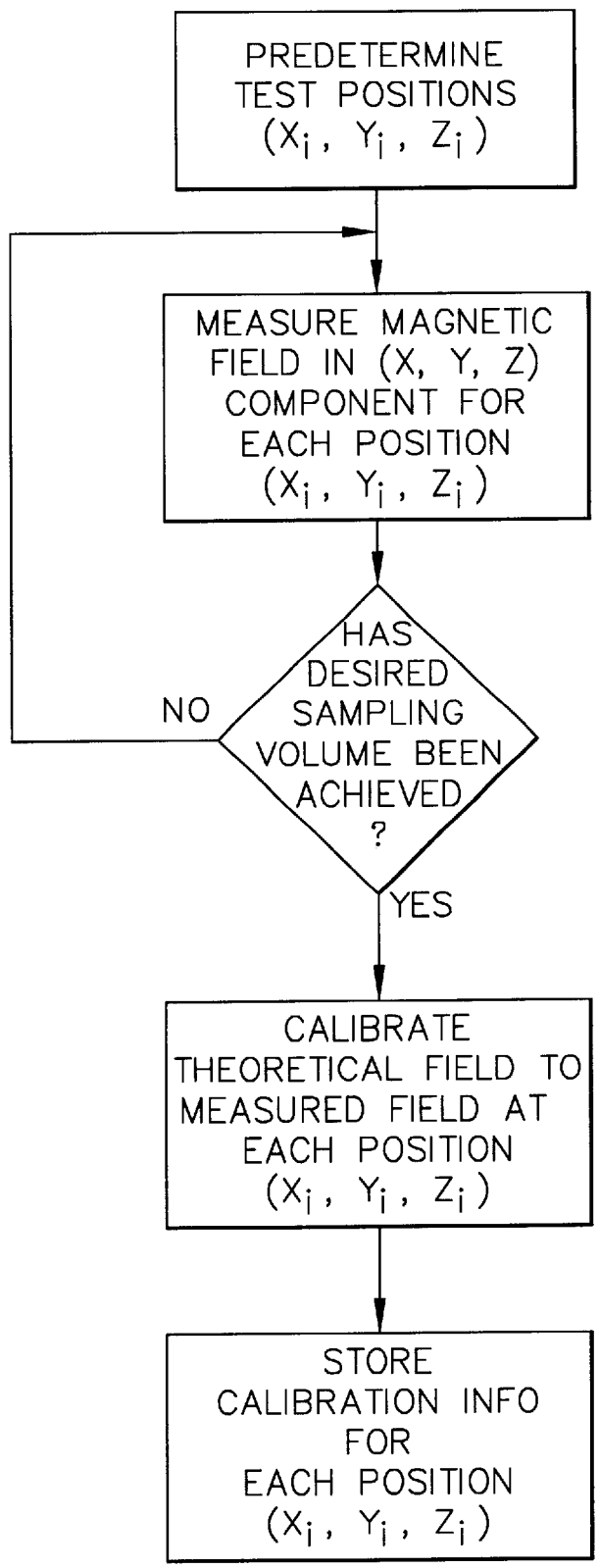
FIG. 6 is a schematic flow chart showing a method of the calibration system of FIG. 5.

FIG. 6 shows a schematic flow chart for the calibration method according to the present invention. Accordingly, with this calibration method, the predetermined test positions for the operating volume are stored in the processor 25. Although one hundred and fifty (150) test positions are preferably utilized, any number of test positions may be utilized depending on the size of the operating volume desired and the degree of accuracy determined necessary. As mentioned above, these test positions ($X_i$, $Y_i$, $Z_i$) substantially conform to the operating volume, for instance, 20 cm×20 cm×20 cm or (20 cm)$^3$. As defined herein, the terms "mapping volume", "sampling volume" and "mapping area" are analogous terms for "operating volume" and are used interchangeably throughout this disclosure.

First the radiator coils of radiators or generators 56, 58 and 60 of the position system 20 are activated through simultaneous energizing using a frequency multiplexing technique in order to create nine distinct magnetic fields (quasi-stationary magnetic fields) and establish the operating volume. Then the robot arm 110 is guided and accurately positioned at each respective test position $(X_i, Y_i, Z_i)$ and the X,Y and Z components of the magnetic field are measured at the test position sensor 100. After each measurement, the processor 25 checks the sampling of these test positions in order to determine if a requisite sampling volume has been achieved. The sampling volume corresponds to the operating volume of the field radiators 56, 58 and 60. Once the desired sampling volume has been completed, the processor 25 correlates the known theoretical magnetic fields at each test position $(X_i, Y_i, Z_i)$ to the actual measured field at each test position $(X_i, Y_i, Z_i)$. This correlation is a mathematical transformation that maps the theoretical magnetic fields at the acquired points $(X_i, Y_i, Z_i)$ to the measured fields at these test points $(X_i, Y_i, Z_i)$. Thus, this correlation is a mapping calculation and the results are stored in the processor 25 for each position $(X_i, Y_i, Z_i)$ and are recalled during a position and orientation sensing procedure such as that previously described, for example, with the system 20 depicted in FIG. 1. The calibration data from these stored calibration files is used to correct the theoretical magnetic fields.

One example of the calibration method employing the calibration system 90 (FIG. 5) is outlined below. As shown, using the calibration system 90, the X, Y, Z components of the magnetic field is measured using the three-axis test position sensor 100 comprising three orthogonal sensor coils 102, 104 and 106 which provide sensor signal information to the processor 25 of the position system 20. In order to calculate the mapping between the location pad fields and the theoretical fields, one needs to know the exact coordinates of the measurement with respect to each of the coils 32, 34, 36, 38, 40, 42, 44, 46 and 48 respectively of the location pad 61. To this end, the robot arm 110 is aligned with the location pad coordinate system, e.g. the sampling volume, using the predefined test positions $(X_i, Y_i, Z_i)$. One acceptable sequence is as follows:

a) Bring the robot arm 110 to a specified test position $X_0, Y_0, Z_0$ which is a test position for measuring relative to the Z coil 106 of the test position sensor 100.

b) Take a measurement of the magnetic field of the Z component using the Z coil 106 of the test position sensor 100.

c) Step the robot arm 110 such that the test position sensor 100 is moved 1 cm forward (this places Y coil 104 at the same point previously occupied by the Z coil 106)=and measure the magnetic field of the Y component using Y coil 104 of the test position sensor 100.

d) Step the robot arm 110 such that the test position sensor 100 is again moved 1cm forward (placing the×coil 102 at the point previously occupied by the Z coil 106 during the first measurement and by the Y coil 104 during the second measurement) and measure the magnetic field of the X component using X coil 102 of the test position sensor 100.

As mentioned above, a typical calibration process is performed in a sampling volume of 20 cm×20 cm×20 cm around the center and above the location pad 61 which corresponds to the operating volume when the system 20 (FIGS. 1 and 2) is used for medical purposes. Additionally, the steps between two successive points/positions are 2–3 cm in each direction though the steps need not be constant through all of the sampling volume. Typically, there are one hundred and fifty (150) points sampled in the entire sampling volume. Thus, at the end of the calibration method, we have:

$$\{\vec{B}^i{}_j | j=1 \ldots 9, i=1 \ldots \approx 150\}$$

Where the i index is the number of points index and j is the frequency index for each generator coil at distinct frequencies. Thus, the index i refers to the measured fields for all of the test positions, e.g. 150.

The mathematical transformation is outlined below. We assume that at any given region of space there exists a rotation transformation between the measured fields and the theoretical fields. Thus, we can rely on the equation:

$$OB_{Th} = B_M \qquad (6)$$

whereby O is a 3×3 rotation matrix that is given by the equation:

$$O = B_M B_{th}^{-1} \qquad (7)$$

It is important to note that both $B_m$ and $B_{th}$ are [3×150] matrices and the mathematical transformation maps $B_m$ and $B_{th}$ as close as possible in the least mean square sense. Also, note that in equation (7), we assumed that the same transformation is applied to the entire space volume. In fact, we may have a separate rotation matrix to each subvolume of our mapping space. For instance, one can divide the mapping volume into sub-cubes having a subvolume of 5 cm×5 cm×5 cm, e.g. each sub-cube being (5 cm)$^3$ and calculate the rotation matrix which is relevant to each of the sub-cubes. This rotation matrix is then stored in the signal processor 25 with the calibration information regarding its position in space. This procedure is conducted for each radiator coil 32, 34, 36, 38, 40, 42, 44, 46 and 48. Typically, one can derive approximately twenty (20)–thirty (30) 3×3 matrices for each coil 32, 34, 36, 38, 40, 42, 44, 46 and 48.

Accordingly, if one were to begin at a starting point $\vec{x}$, then the theoretical field at the point $\vec{B}_{th}(\vec{x})$ can be calculated by the algorithm of the present invention. Then, the "new" theoretical field is given by the expression:

$$O(\vec{x})B(\vec{x})$$

Where o(x) is the relevant transformation at the point x. And for the calculated theoretical Jacobean to be J(x), then the "new" calibrated Jacobean is given by the equation:

$$O(x)J(x)$$

Accordingly, both the calibrated B (magnetic field) and J (Jacobean) are used in the algorithm of the present invention in the same manner that noncalibrated versions are used. However, with the added calibration information (the calibrated B), the system 20 has greater position accuracy which is particularly useful in medical procedures.

Calibration Method with Static Metal Compensation

The present invention also includes a novel calibration method for the radiators 56, 58 and 60 of the position and orientation system 20 (FIG. 1) capable of compensating for the effects of disturbances caused by nonmoving or static metallic objects placed within the mapping or operating volume. The calibration method is used in conjunction with the calibration system 90 shown in FIG. 5 including the robot arm 110 to ensure accuracy. Moreover, this calibration method is useful for various arrangements of the radiators 56, 58 and 60 to include the radiator arrangement embodiments shown in FIGS. 5, 7, 8 and 9.

Accordingly, a metallic object (not shown), such as the C-arm of a fluoroscopic device, is placed within the intended mapping volume generated by the radiators 56, 58 and 60. The purpose of this step is to establish calibration data for storage in the signal processor 25 that takes into account the disturbance effects provided by the metallic object on the magnitude and direction of the magnetic fields generated by the radiator coils 32, 34, 36, 38, 40, 42, 44, 46 and 48 of the radiators 56, 58 and 60 respectively.

As mentioned above, a preferred mapping volume is the magnetic field inside an area approximately 20 cm×20 cm×20 cm or (20 cm)$^3$. The calibration method according to the present invention takes into account the magnetic field produced by any metal object located within the mapping volume. Once the magnetic field is mapped according to the method of the present invention described in greater detail below, for instance, using the single-axis sensor algorithm associated with the system 20 (FIG. 1), one can use the system 20, even in the presence of one or more metallic objects, as if it was a completely undisturbed magnetic field situation, i.e. a situation without the presence of metallic object interference.

Figure 12:
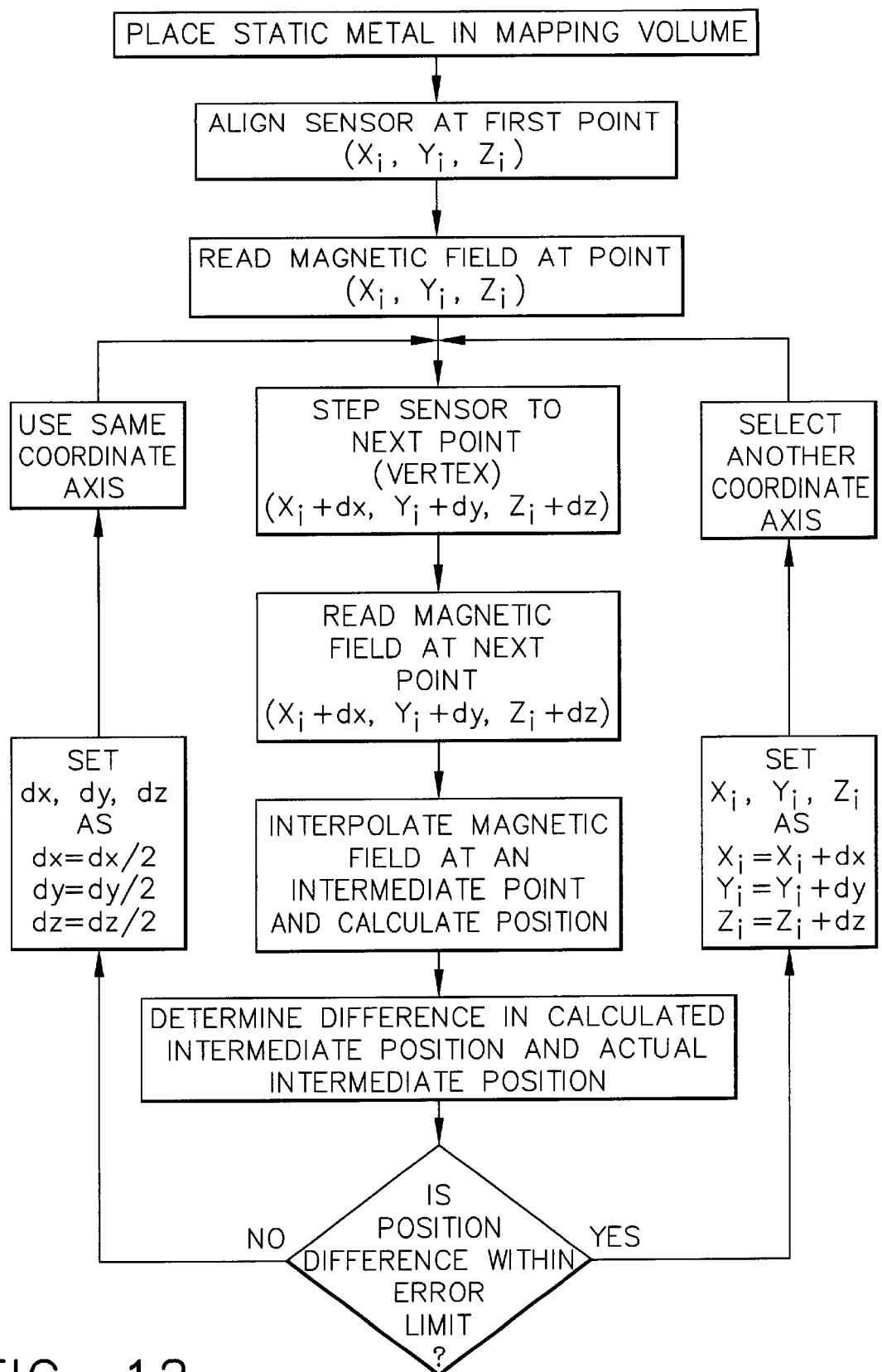
FIG. 12 is a schematic flow chart illustrating one embodiment of a novel calibration method for accounting for the effects of nonmoving metallic objects utilizing the calibration system of FIG. 5.

One embodiment of the method according to the present invention is best illustrated in the schematic flow chart of FIG. 12. First, an intended mapping volume is defined and one or more static metallic objects are placed within the intended mapping volume. Again, these metallic objects would be those objects located within the sterile field of the patient and within the mapping volume. One example of a typical nonmoving (nonmoving meaning only relative to the location pad) metallic object is the C-arm of a fluoroscopic device. Accordingly, the C-arm is placed within the mapping volume.

Figure 11:
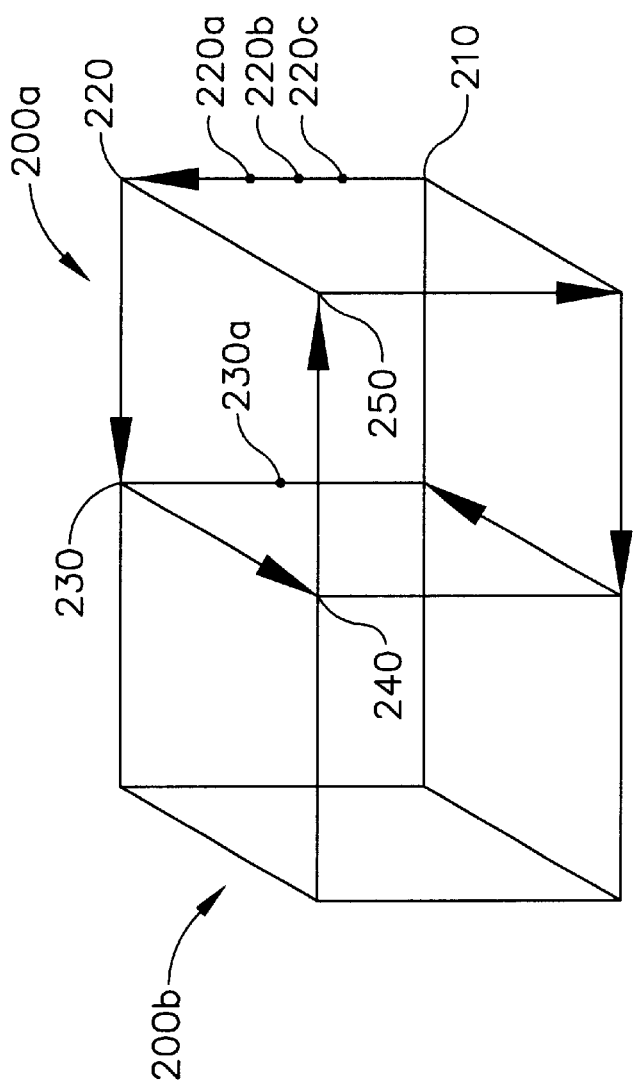
FIG. 11 is a schematic illustration of a calibration cube utilized in a novel calibration method for the calibration system of FIG. 5.

Turning now to FIGS. 5 and 11, the robot arm 110 moves the position sensor 100 to a starting point to begin a mapping and calibration procedure by creating a mapping calibration cube 200a. For example, the starting point is a position or point beginning at the vertex of a cube having a volume of (3 cm)$^3$. For example, an appropriate first point or starting position is the point 210 of the cube 200a shown in FIG. 11.

The sensor 100 is aligned at the first point or coordinate position 210 represented according to three dimensional coordinate ($X_i$, $Y_i$, $Z_i$) within the mapping calibration cube 200a (within the mapping volume) and the magnetic field of the radiator coils 32, 34, 36, 38, 40, 42, 44, 46, 48 is read and measured at the first point to establish the first coordinate position 210 with the sensor 100 through the signal processor 25. The sensor 100 is then stepped or moved to a next or second point 220 ($X_i$+dx, $Y_i$+dy, $Z_i$+dz) defined by the first position and an added distance component (dx, dy, dz) by the robot arm 110. The magnetic field at the second point 220 is then read and measured through the signal processor 25 to establish a next or second coordinate position.

The signal processor is preprogrammed with the calibration positions of the calibration cube 200a which are the vertices (210, 220, 230, 240, 250, etc.) of a (3 cm)$^3$ volume cube. The robot arm 110 steps the sensor 100 in incremental predetermined distances ranging between 2–3 cm (preferably the stepped distance is 3 cm). The exact step distance is predetermined and remains constant throughout this calibration mapping procedure with the only exception being where accounting for metallic disturbance effects at a particular position. This modification to step distance is specifically addressed below.

For example, for the procedure schematically illustrated in FIG. 11, the step distance is 3cm (along one of the coordinate axes X, Y or Z) for each vertex point or position 210, 220, 230, 240 and 250. Additionally, the robot arm 110 steps the sensor 100 according to the direction of the arrows along the edges of the cube 200a (along each coordinate axis).

Once the magnetic field is measured and the position determined at the first point 210, e.g. first coordinate position ($X_i$, $Y_i$, $Z_i$) and at the next or second point 220, e.g. next or second coordinate position ($X_j$=$X_i$+dx, $Y_j$=$Y_i$+dy, $Z_j$=$Z_i$+dz), reflecting the added distance component dx, dy, dz where dx=3 cm (also referred to as the step or stepped distance), the magnetic field at an intermediate point 220a between the first position 210 and the second position 220 is interpolated and the position coordinate of the intermediate point 220a is calculated by the signal processor 25. It is important to note that the intermediate point 220a will lie along the coordinate axis of the stepped distance, for instance, within a 3 cm distance along the x coordinate axis between vertice points 210 and 220.

After interpolating the magnetic field of the intermediate point 220a and calculating the position of the intermediate point (calculated intermediate position using the position and orientation algorithm), the signal processor 25 takes the difference between the calculated intermediate position and the actual intermediate position. The intermediate position difference ($\epsilon$) is then compared to an error limit also prestored in the signal processor 25. Although the error limit may be any value, an error limit $\leq 1$ mm has been found to be reasonable and an acceptable error limit.

The next or second point ($X_j$, $Y_j$ $Z_j$) is then set as ($X_j$=$X_i$+dx, $Y_j$=$Y_i$+dy, $Z_j$=$Z_i$+dz) by the signal processor 25 if the position difference ($\epsilon$) is within the error limit ($\leq 1$ mm) and the robot arm 110 steps the sensor 100 to another point 230, e.g. a third or another next point (third coordinate position along another coordinate axis, e.g. Y axis (third vertex of cube 200a along step distance dy=3 cm).

If the intermediate position difference ($\epsilon$) is not within the error limit, e.g. $\epsilon$ is not $\leq 1$ mm, the signal processor 25 decreases the value of the added distance component, e.g. sets dx, dy, dz as dx=dx/2, dy=dy/2, dz=dz/2. For example, the added distance component dx is decreased to 1.5 cm (3 cm÷2 cm and whereby dy=dz=0) and the robot arm 110 repeats the step to a new second point 220b along the same coordinate axis, e.g. X axis. Accordingly, the sensor 100 is stepped an added distance component of dx=1.5 cm to the new second point/vertice 220b whereby the magnetic field is read at point 220b and its position is determined (new second coordinate position). The magnetic field is then interpolated for a new intermediate point 220c, e.g. a point/position between the new second position 220b and the first position 210 and the position of the intermediate point 220c is calculated (new intermediate position) using the position and orientation algorithm. And, just as before, the new intermediate calculated position is compared to the actual position of the intermediate point 220c to determine if this difference ($\epsilon$) is within the error limit ($\leq 1$ mm). If the position difference ($\epsilon$) is within the error limit, the robot arm steps the sensor 100 to yet another point vertice 230*a* (position vertice) of the cube 200*a* along another coordinate axis, e.g. Y axis by the added distance component dy=3 cm and repeats the steps outlined above for each vertice of cube 200*a*.

As mentioned above, the added distance component of the intermediate point is set by decreasing the value of the added distance component if the position is not within the error limit. The method steps are repeated after making the decreased adjustment to the added distance component.

This calibration mapping process accounting for static metal compensation is continued according to a series or plurality of created mapping calibration cubes beginning with the mapping of a second adjacent cube 200*b* until the complete mapping volume of 20 cm×20 cm×20 cm or (20 cm)$^3$ is completely mapped and calibrated accounting for existing metallic objects within the mapping volume. It is important to note that each of the mapping calibration cubes 200*a*, 200*b*, etc. may very well be cubes having sides that are not of equal lengths due to the effects of a metallic object encountered during the mapping of a particular cube.

Figure 13:
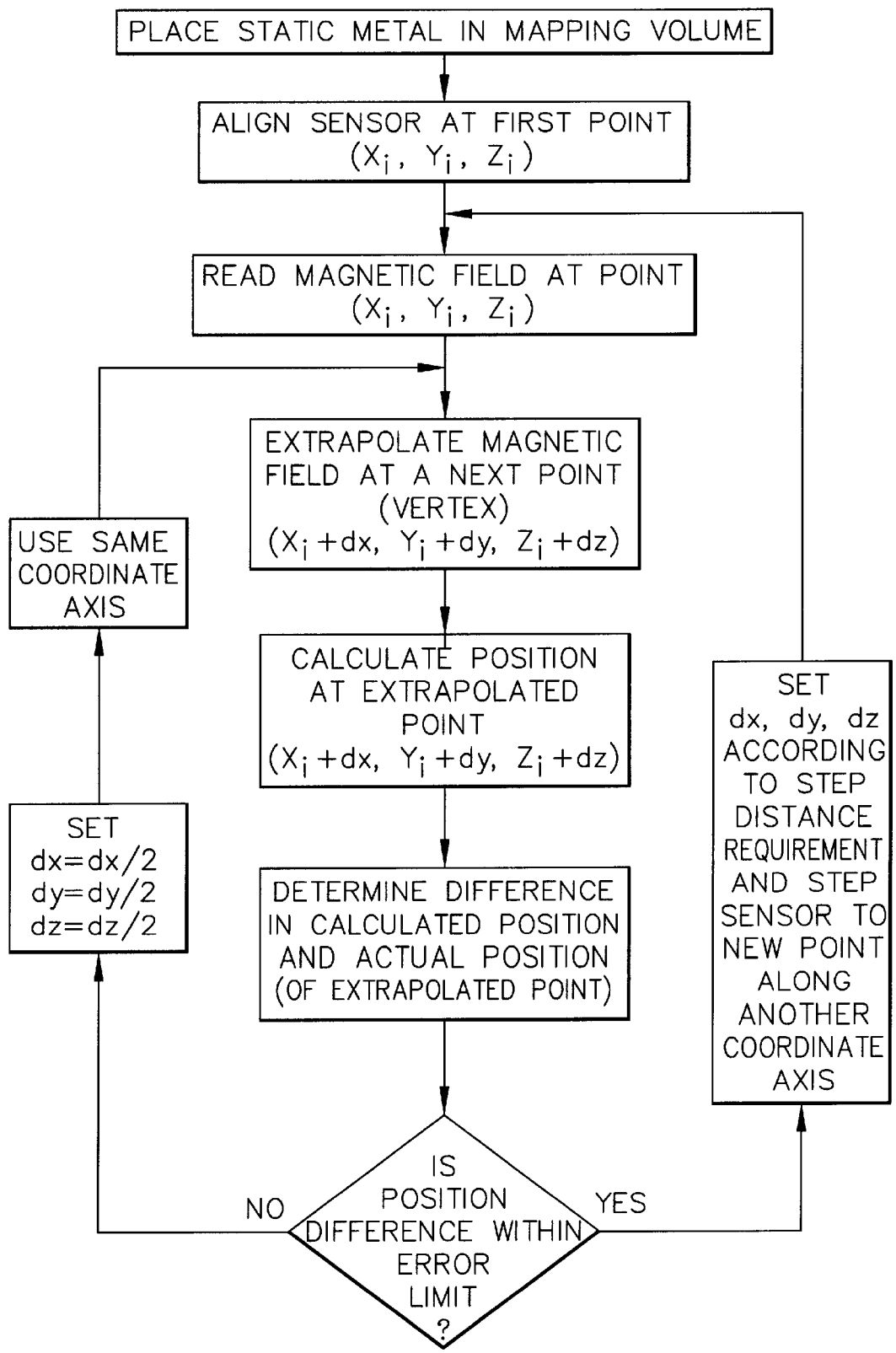
FIG. 13 is a schematic flow chart illustrating a second embodiment of a novel calibration method for accounting for the effects of nonmoving metallic objects utilizing the calibration system of FIG. 5.

A second embodiment of the calibration method according to the present invention utilizes extrapolation of the magnetic field at the next point. As shown in FIG. 13, in particular, first, the metallic object is placed within the intended mapping volume. Again, the robot arm 110 positions the sensor 100 at the first point 210 (starting or first position $X_i, Y_i, Z_i$) and the magnetic field at this first point is read and measured by the signal processor 25 to determine the first coordinate position. Next, the signal processor 25, extrapolates the magnetic field at the next or second point 220, e.g. next or second coordinate position (next vertex of mapping cube 200*a* which is the extrapolated point) defined as ($X_i=X_i+dx$, $Y_i=Y_i+dy$, $Z_i=Z_i+dz$) which includes the added distance component dx, dy, dz as appropriate. In this case, the added distance component (dx) is a 3 cm distance along the X coordinate axis.

Once the magnetic field for the second point (the next point) is extrapolated, the location coordinate of this point 220 (calculated second position) is calculated using the position and orientation algorithm and compared to the actual position coordinate of the second point 220 in order to determine the position difference ($\epsilon$). If the position difference ($\epsilon$) is within the predefined error limit stored in the signal processor 25, the robotic arm 110 moves the sensor 100 to a new point 230 (next vertice) along another coordinate axis, e.g. Y axis and the steps above are continued along the Y coordinate axis, etc. If the position difference ($\epsilon$) is not within the error limit of 1 mm, the magnetic field is extrapolated for an intermediate point 220*b*, e.g. intermediate position coordinate ($X_i+dx/2, Y_i+dy/2, Z_i+dz/2$) between the second point 220, e.g. second coordinate position and the first point 210, e.g. first coordinate position (still along the same coordinate axis). Although, in this example, the added distance component dx is decreased by a factor of two (2), any sufficient factor to decrease the added distance component will suffice. A magnetic field measurement is then taken at the intermediate point 220*b* with the sensor 100 and signal processor 25 in order to determine the intermediate position coordinate using the position and orientation algorithm. From the intermediate position 220*b* (which is actually a new second or next point), the rest of the steps are followed in sequence which includes determining the position difference ($\epsilon$) of the intermediate point 220*b* (new second point) and determining whether $\epsilon \leq 1$ mm.

The mapping calibration procedure is continued in accordance with the method steps shown in FIG. 13 thereby creating new mapping cubes 200*b*, etc. until the entire mapping volume is completed (approximately 20 cm×20 cm×20 cm or (20 cm)$^3$ volume).

It is clearly contemplated by the present invention that the steps of the methods and algorithms outlined throughout this disclosure may be sequenced differently than the sequences described above which served for example purposes only. It is clearly contemplated that the sequencing of these steps may be alternated and, in some instances, optionally deleted and still satisfy the novel requirements of the present invention.

It will be appreciated that the preferred embodiments described above are cited by way of example and the full scope of the invention is limited only by the claims, which follow.

What is claimed is:

1. A system for determining the position of a medical device having a sensor, said system comprising:

a plurality of field radiators, each field radiator having a plurality of radiator elements, each radiator element generating an electromagnetic field distinct from one another through simultaneous energizing of said radiator elements;

a signal processor operatively connected to said field radiators and said sensor of said medical device, said signal processor receiving a sensing signal from said sensor indicative of the electromagnetic field sensed at said sensor, said sensing signal defining a measured electromagnetic field at said sensor, said signal processor also having a desired range of accuracy for said system stored therein, said signal processor including:

(a) an initial position estimator for establishing an initial position estimate for said sensor;

(b) a magnetic field calculator for calculating the electromagnetic field at said initial position estimate;

(c) a steepest descent calculator for calculating a steepest descent of said calculated electromagnetic field to said measured electromagnetic field; and (d) a new position estimate calculator for calculating a new position estimate of said sensor based on said steepest descent;

wherein said signal processor determines said position of said sensor when said new position estimate of said sensor is within said desired range of accuracy.

2. The system according to claim 1, wherein said signal processor includes pre-stored calibration information.

3. The system according to claim 1, wherein said desired range of accuracy is $\leq 0.0001$ cm.

4. The system according to claim 2, wherein said desired range of accuracy is $\leq 0.0001$ cm.

5. The system according to claim 1, wherein said field radiators are arranged in a fixed arrangement.

6. The system according to claim 5, wherein said signal processor determines a position and orientation of said sensor.

7. The system according to claim 6, wherein said position is in three different directions (X, Y, Z) and at least two orientations (pitch and yaw).

8. The system according to claim 7, wherein said radiator elements of said field radiators are mutually orthogonal.

9. The system according to claim 7, wherein said radiator elements of said field radiators are not mutually orthogonal.

10. The system according to claim 8, wherein said radiator elements of said field radiators are not co-located.

11. The system according to claim 9, wherein said radiator elements of said field radiators are not co-located.

12. The system according to claim 8, wherein said radiator elements of said field radiators are co-located.

13. The system according to claim 9, wherein said radiator elements of said field radiators are co-located.

14. The system according to claim 7, wherein said system further comprises a display operatively connected to said signal processor for displaying said position and said orientation of said sensor.

15. The system according to claim 14, wherein said display displays said position and said orientation of said sensor with respect to an anatomical feature of a patient.

16. The system according to claim 15, wherein said system further comprises a reference device for establishing a frame of reference.

17. A system for determining the position of a medical device having a sensor, said system comprising:
   a plurality of field radiators, each field radiator having a plurality of radiator elements, each radiator element generating an electromagnetic field distinct from one another through simultaneous energizing of said radiator elements;
   a signal processor operatively connected to said field radiators and said sensor of said medical device, said signal processor receiving a sensing signal from said sensor indicative of the electromagnetic field sensed at said sensor, said sensing signal defining a measured electromagnetic field at said sensor, said signal processor also having a desired range of accuracy for said system stored therein, said signal processor including:
      (a) an initial position estimator for establishing an initial position estimate for said sensor;
      (b) a magnetic field calculator for calculating the electromagnetic field at said initial position estimate;
      (c) a global converger for determining the minimum field at said sensor based on a direction of the initial position estimate; and
      (d) a new position estimate calculator for calculating a new position estimate of said sensor based on said steepest descent;
   wherein said signal processor determines said position of said sensor when said new position estimate of said sensor is within said desired range of accuracy.

18. The system according to claim 17, wherein said signal processor includes pre-stored calibration information.

19. The system according to claim 18, wherein said desired range of accuracy is $\leq 0.0001$ cm.

20. A method of determining the position and orientation of a sensor relative to a plurality of field radiators of known location, each of said field radiators comprising a plurality of co-located radiator elements, each radiator element generating an electromagnetic field distinct from one another through simultaneous energizing of said radiator elements, said sensor producing sensing signals indicative of a measured electromagnetic field at said sensor, said method comprising the steps of:
   (a) establishing a desired range of accuracy;
   (b) determining an initial estimate of sensor position and orientation;
   (c) calculating an electromagnetic field at the estimated sensor position and orientation;
   (d) calculating the steepest descent from the calculated electromagnetic field at the estimated sensor position and orientation to the measured electromagnetic field at the sensor;
   (e) calculating a new estimate for said sensor position and orientation from said steepest descent;
   (f) iterating steps (c)–(e) based on said newly calculated sensor position and orientation estimate of step (e) to refine the sensor position and orientation estimate.

21. The method according to claim 20, wherein said desired range of accuracy is $\leq 0.0001$ cm.

22. The method according to claim 21, including establishing and storing calibration information for said field radiators.

23. The method according to claim 22, wherein said calibration information is used at steps (c) and (d) for calculating a new estimate for said sensor position and orientation.

24. The method according to claim 23, including refining said initial estimate of sensor position and orientation using a dipole approximation after step (b).

25. The method according to claim 24, including determining the position of said sensor in three different directions (X,Y,Z) and orientation of said sensor in at least two orientations (pitch and yaw).

26. The method according to claim 25, including displaying said position and orientation of said sensor.

27. The method according to claim 26, including displaying said position and orientation of said sensor with respect to an anatomical feature of a patient.

28. A method of determining the position and orientation of a sensor relative to a plurality of field radiators of known location, each of said field radiators comprising a plurality of co-located radiator elements, each radiator element generating an electromagnetic field distinct from one another through simultaneous energizing of said radiator elements, said sensor producing sensing signals indicative of a measured electromagnetic field at said sensor, said method comprising the steps of:
   (a) establishing a desired range of accuracy;
   (b) determining an initial estimate of sensor position and orientation;
   (c) calculating an electromagnetic field at the estimated sensor position and orientation;
   (d) determining a minimum electromagnetic field at said sensor based on a direction of the initial position estimate using a global convergent technique;
   (e) calculating a new estimate for said sensor position and orientation based on said minimum electromagnetic field;
   (f) iterating steps (c)–(e) based on said newly calculated sensor position and orientation estimate of step (e) to refine the sensor position and orientation estimate.

29. The method according to claim 28, wherein said desired range of accuracy is $\leq 0.0001$ cm.

30. The method according to claim 29, including establishing and storing calibration information for said field radiators.

31. The method according to claim 30, wherein said calibration information is used at steps (c) and (d) for calculating a new estimate for said sensor position and orientation.

\* \* \* \* \*